(12) United States Patent
Tada et al.

(10) Patent No.: US 7,516,020 B2
(45) Date of Patent: Apr. 7, 2009

(54) PARTICULATES DETECTION METHOD

(75) Inventors: Junji Tada, Matsuyama (JP); Hideyuki Kurokawa, Touyo (JP); Yoshiyuki Fujii, Onsen-gun (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 11/727,761

(22) Filed: Mar. 28, 2007

(65) Prior Publication Data

US 2007/0174018 A1    Jul. 26, 2007

Related U.S. Application Data

(62) Division of application No. 10/959,086, filed on Oct. 7, 2004, now Pat. No. 7,430,480.

(30) Foreign Application Priority Data

Oct. 7, 2003  (JP)  ............... 2003-348787
Oct. 8, 2003  (JP)  ............... 2003-349981

(51) Int. Cl.
*G01N 31/00* (2006.01)

(52) U.S. Cl. ........................................ 702/29

(58) Field of Classification Search ................. 702/29; 356/237.4, 39
See application file for complete search history.

(56) References Cited

U.S. PATENT DOCUMENTS 3,963,350 A * 6/1976 Watanabe et al. ............. 356/39
4,957,363 A   9/1990 Takeda et al.
6,411,377 B1 * 6/2002 Noguchi et al. .......... 356/237.4

FOREIGN PATENT DOCUMENTS

JP    2000-287077    10/2000

* cited by examiner

*Primary Examiner*—Tung S Lau
*Assistant Examiner*—Xiuquin Sun
(74) *Attorney, Agent, or Firm*—Wenderoth, Lind & Ponack, L.L.P.

(57) ABSTRACT

A particulate determination method determines by onetime scanning, the size of a particulate included in a plurality of particulates of various sizes which are arranged on a disc. False recognition of the number of particulates is avoided even when a plurality of particulates are adjacent to each other. A photodector detection signal is judged using plural threshold values according to the sizes of particulates to be detected. Results of determinations corresponding to the respective threshold values are stored on mutually independent memory maps. When counting particulates, a particulate size and a particulate count value are determined from a combination of stored data appearing in a scanning window at the same position on the respective memory maps.

7 Claims, 21 Drawing Sheets

| type of particulate | threshold a4 | threshold a3 | threshold a2 | threshold a1 |
|---|---|---|---|---|
| A | 0 | 0 | 0 | 1 |
| B | 0 | 0 | 1 | 3 |
| C | 0 | 1 | 3 | 5 |

Fig.5(a)

|   |   |   |   |   |   |   |   |   |   |
|---|---|---|---|---|---|---|---|---|---|
| 0 | 0 | 0 | 0 | 0 | 0 | 0 | 0 | 0 | 0 |
| 0 | 0 | 0 | 0 | 1 | 0 | 0 | 0 | 0 | 0 |
| 0 | 0 | 0 | 0 | 1 | 0 | 0 | 0 | 0 | 0 |
| 0 | 0 | 0 | 0 | 0 | 1 | 0 | 0 | 0 | 0 |
| 0 | 0 | 0 | 0 | 0 | 0 | 1 | 0 | 0 | 0 |
| 0 | 0 | 0 | 0 | 0 | 1 | 0 | 0 | 0 | 0 |
| 0 | 0 | 0 | 0 | 1 | 0 | 0 | 0 | 0 | 0 |
| 0 | 0 | 0 | 0 | 1 | 0 | 0 | 0 | 0 | 0 |
| 0 | 0 | 0 | 0 | 1 | 0 | 0 | 0 | 0 | 0 |
| 0 | 0 | 0 | 0 | 0 | 1 | 0 | 0 | 0 | 0 |
| 0 | 0 | 0 | 0 | 1 | 0 | 0 | 0 | 0 | 0 |
| 0 | 0 | 0 | 0 | 1 | 0 | 0 | 0 | 0 | 0 |
| 0 | 0 | 0 | 0 | 0 | 0 | 0 | 0 | 0 | 0 |

|   |   |   |   |   |   |   |   |   |   |
|---|---|---|---|---|---|---|---|---|---|
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 1 | 0 | 0 | 0 | 0 | 0 |
| 0 | 0 | 0 | 0 | 0 | 1 | 0 | 0 | 0 | 0 |
| 0 | 0 | 0 | 0 | 1 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 1 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |

| 0 | 0 | 0 | 0 | 0 | 0 | 0 | 0 | 0 | 0 |
|---|---|---|---|---|---|---|---|---|---|
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 1 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |

| 0 | 0 | 0 | 0 | 0 | 0 | 0 | 0 | 0 | 0 |
|---|---|---|---|---|---|---|---|---|---|
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |

| memory array | A1 | A2 | A3 | A4 |
|---|---|---|---|---|
| OR of row | 1 | 0 | 0 | 0 |
| | 1 | 0 | 0 | 0 |
| | 1 | 1 | 0 | 0 |
| | 1 | 1 | 1 | 0 |
| | 1 | 1 | 0 | 0 |
| | 1 | 0 | 0 | 0 |
| | 1 | 0 | 0 | 0 |
| | 1 | 0 | 0 | 0 |
| | 1 | 1 | 0 | 0 |
| | 1 | 0 | 0 | 0 |
| | 1 | 0 | 0 | 0 | count condition

| particulate A | 0 |
|---|---|
| particulate B | 0 |
| particulate C | 0 |

Fig.6(b)

| memory array | A1 | A2 | A3 | A4 |
|---|---|---|---|---|
| OR of row | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 1 | 0 | 0 | 0 |
| | 1 | 0 | 0 | 0 |
| | 1 | 0 | 0 | 0 |
| | 1 | 1 | 0 | 0 |
| | 1 | 0 | 0 | 0 |
| | 1 | 0 | 0 | 0 | count condition

| particulate A | 0 |
|---|---|
| particulate B | 0 |
| particulate C | 1 |

Fig.6(c)

| memory array | A1 | A2 | A3 | A4 |
|---|---|---|---|---|
| OR of row | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 1 | 0 | 0 | 0 |
| | 1 | 0 | 0 | 0 |
| | 1 | 0 | 0 | 0 | count condition

| particulate A | 0 |
|---|---|
| particulate B | 1 |
| particulate C | 1 |

Fig.6(d)

| memory array | A1 | A2 | A3 | A4 |
|---|---|---|---|---|
| OR of row | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 |
| | 0 | 0 | 0 | 0 | count condition

| particulate A | 3 |
|---|---|
| particulate B | 1 |
| particulate C | 1 |

Fig.11(a)

| memory array | B1 | B2 |
|---|---|---|
| OR of row | 1 | 0 |
| | 1 | 0 |
| | 1 | 1 |
| | 1 | 1 |
| | 1 | 1 |
| | 1 | 0 |
| | 1 | 0 |
| | 1 | 0 |
| | 1 | 1 |
| | 1 | 0 |
| | 1 | 0 | count condition

| particulate D | 0 |
|---|---|
| particulate E | 0 |
| particulate F | 0 |

Fig.11(b)

| memory array | B1 | B2 |
|---|---|---|
| OR of row | 0 | 0 |
| | 0 | 0 |
| | 0 | 0 |
| | 0 | 0 |
| | 0 | 0 |
| | 1 | 0 |
| | 1 | 0 |
| | 1 | 0 |
| | 1 | 1 |
| | 1 | 0 |
| | 1 | 0 | count condition

| particulate D | 0 |
|---|---|
| particulate E | 0 |
| particulate F | 1 |

Fig.11(c)

| memory array | B1 | B2 |
|---|---|---|
| OR of row | 0 | 0 |
| | 0 | 0 |
| | 0 | 0 |
| | 0 | 0 |
| | 0 | 0 |
| | 0 | 0 |
| | 0 | 0 |
| | 0 | 0 |
| | 1 | 0 |
| | 1 | 0 |
| | 1 | 0 | count condition

| particulate D | 0 |
|---|---|
| particulate E | 1 |
| particulate F | 1 |

Fig.11(d)

| memory array | B1 | B2 |
|---|---|---|
| OR of row | 0 | 0 |
| | 0 | 0 |
| | 0 | 0 |
| | 0 | 0 |
| | 0 | 0 |
| | 0 | 0 |
| | 0 | 0 |
| | 0 | 0 |
| | 0 | 0 |
| | 0 | 0 |
| | 0 | 0 | count condition

| particulate D | 3 |
|---|---|
| particulate E | 1 |
| particulate F | 1 |

Fig.15

|    | 1 | 2 | 3 | 4 | 5 | 6 | 7 |
|----|---|---|---|---|---|---|---|
| 1  | 0 | 0 | 0 | 0 | 0 | 0 | 0 |
| 2  | 0 | 0 | 0 | 0 | 0 | 0 | 0 |
| 3  | 0 | 0 | 0 | 0 | 0 | 0 | 0 |
| 4  | 0 | 0 | 0 | 0 | 0 | 0 | 0 |
| 5  | 0 | 0 | 0 | 0 | 0 | 0 | 0 |
| 6  | 0 | 0 | 0 | 1 | 0 | 0 | 0 |
| 7  | 0 | 0 | 0 | 0 | 0 | 0 | 0 |
| 8  | 0 | 0 | 0 | 0 | 0 | 0 | 0 |
| 9  | 0 | 0 | 0 | 0 | 0 | 0 | 0 |
| 10 | 0 | 0 | 0 | 1 | 0 | 0 | 0 |
| 11 | 0 | 0 | 0 | 1 | 0 | 0 | 0 |
| 12 | 0 | 0 | 0 | 1 | 0 | 0 | 0 |
| 13 | 0 | 0 | 0 | 1 | 0 | 0 | 0 |
| 14 | 0 | 0 | 0 | 1 | 0 | 0 | 0 |
| 15 | 0 | 0 | 0 | 0 | 0 | 0 | 0 |
| 16 | 0 | 0 | 0 | 0 | 0 | 0 | 0 |

Fig.23(b)

| 0 | 0 | 0 | 0 | 0 | 0 | 0 | 0 | 0 | 0 | 0 | 0 |
|---|---|---|---|---|---|---|---|---|---|---|---|
| 0 | 0 | 1 | 1 | 0 | 0 | 0 | 1 | 0 | 0 | 0 | 0 |
| 0 | 0 | 1 | 1 | 0 | 1 | 0 | 0 | 0 | 0 | 0 | 0 |
| 0 | 1 | 1 | 0 | 0 | 1 | 0 | 1 | 0 | 0 | 0 | 0 |
| 0 | 0 | 0 | 0 | 0 | 0 | 0 | 0 | 0 | 0 | 0 | 0 |
| 0 | 0 | 0 | 1 | 1 | 0 | 1 | 0 | 0 | 0 | 0 | 0 |
| 0 | 0 | 1 | 1 | 0 | 1 | 0 | 1 | 0 | 0 | 0 | 0 |
| 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 |

PARTICULATES DETECTION METHOD

This is a divisional application of U.S. patent application Ser. No. 10/959,086, filed Oct. 7, 2004 now U.S. Pat. No. 7,430,480.

BACKGROUND OF THE INVENTION

1. Field of the Invention

The present invention relates to a particulate determination method for correctly determining particulates when counting particulates having sizes within a predetermined range, for each size, among particulates of various sizes, or determining a specific particulate in a specimen that is injected onto an analysis disc, thereby accurately determining the sizes and numbers of the respective particulates.

2. Description of the Related Art

A conventional particulate determination method will be described with reference to FIG. 19(a).

FIG. 19(a) shows a particulate 51 as a target of measurement, tracks 52, and a laser beam 53.

In a conventional analysis device which injects a specimen onto an analysis disc and counts the number of specific particulates existing in the specimen, tracks 52 are spirally carved on the disc like an optical disc such as a CD-ROM, and the laser beam 53 is controlled so as to move on the tracks 52 along the tracks 52 during disc rotation.

On the other hand, the particulate 51 as a target of measurement is larger than the width of the track 52, and it lies over several tracks 52. When the laser moves across the tracks 52, a signal change occurs in a laser beam receptor (Photo Detector, hereinafter referred to as PD) which receives the laser beam 53 that has passed through the disc and performs light-to-electricity conversion, depending on whether the particulate 51 exists on the tracks 52 or not.

When it is judged that a particulate 51 is on the tracks 52 by processing the signal change, "1" is stored in a memory. Otherwise, "0" is stored in the memory. From a data array thus obtained, the length of 1s in the direction of the radius of the disc is detected, thereby to determine the size of the particulate and count the number of the particulates.

As a method for determining the sizes of particulates and counting the number of particulates, there is proposed a method of, using a rectangle scanning window, performing detection while changing the size of the scanning window for each size of a desired particulate (for example, Japanese Published Patent Application No. 2000-287077).

FIG. 19(b) is a diagram for explaining a particulate size determination and counting method using a scanning window.

For example, when detecting a particulate having a size equivalent to 6 tracks from among particulates having sizes equivalent to 1~11 tracks, initially scanning is carried out using a window having a size of 6×X1 while shifting the window one by one in an X direction, and positions in which all rows in the window include "1" are counted.

Next, scanning is carried out using a window having a size of 7×X1 while shifting the window one by one in the X direction, and positions in which all rows include "1" are counted.

Thereby, the number of particulates each lying over six or more tracks and the number of particulates each lying over seven or more tracks are obtained, and the number of particulates each having a size equivalent to six tracks can be obtained from a difference between the numbers.

The X1 is an integer value larger than a position deviation range of "1" due to uneven disc rotation or variations in signal detection. Therefore, even when a position error of "1" occurs in each track, it can be detected as "1" from the same particulate.

Further, FIG. 20(a) is a diagram illustrating particulate detection by another particulate determination method.

An analysis disc has a light reflectivity and permeability, and comprises a base disc in which tracks 201 for guiding or data recording are spirally carved. The analysis disc also has an upper cover having an injection port, and an adhesive layer for bonding the upper cover to the base disc, and forming a flow path.

The outline of the analysis disc is identical to those of optical discs such as CD-ROM and CD-RW except its thickness. When the analysis disc is conveyed into an analysis device, it is chucked with a motor having a turn table, whereby the analysis disc can rotate about the center of the disc diameter.

A specimen for examination is injected into the analysis disc, and passes through the flow path constituted by the adhesive layer, the lower surface of the upper cover, and the upper surface of the base disc, and is subjected to pretreatment such as centrifugal separation utilizing a centrifugal force that is generated by the rotation of the analysis disc. Thus, particulates as measurement target components in the specimen reach an area where measurement should be carried out.

In the measurement area, the particulates in the specimen exist on the surface of the base disc due to an adsorption factor (antibody) that adsorbs specific particulates applied onto the surface of the base disc, and each particulate has a size larger than the width of the track 201 and lies over plural tracks 201 as shown in FIG. 20(a). Therefore, the presence or absence of a particulate on the tracks 201 can be determined by making the laser beam 202 follow the tracks 201 and detect a difference signal of passing light.

To be specific, the analysis device has a two-part split PD for receiving the laser beam 202 that has passed through the analysis disc. The analysis device is located so that a spot of the laser outputted from the optical pickup is positioned in the center of the PD when there is no particulate on the analysis disc.

When a particulate crosses the laser, the position of the laser spot which is positioned in the center of the two-part split PD is changed due to a change in refraction of the beam.

By obtaining a difference between the signals from the two-part split PD, the position change of the laser spot is detected as an S-shaped pattern (hereinafter referred to as an S-shaped curve) having a maximum value and a minimum value according to the size of the measurement target. Consequently, the presence or absence of a particulate on the tracks can be determined by presence/absence of the S-shaped curve.

The difference signal from the two-part split PD is stored in a memory at regular intervals. When the S-shaped curve is detected, it is judged that a particulate 203 exists, and "1" is stored in the memory. Otherwise, "0" is stored in the memory.

During the analysis, the number of particulates should be counted for each size. A size determination and counting are carried out as follows. Using rectangle windows, the memory is scanned while changing the window for each size of particulate to be obtained. The presence or absence of a particulate of the desired size is determined according to presence/absence of a particulate that matches the condition of the window (for example, Japanese Published Patent Application No. 2000-287077).

FIG. 20(b) is a diagram for explaining a particulate determination method using a conventional operation window 204 for particulate size determination.

For example, when detecting a particulate having a size equivalent to 6 tracks from among particulates having various sizes equivalent to 1-11 tracks, initially scanning is carried out using a window having a size of 6×X1 while shifting the window one by one in the X direction as the track direction to detect a position where all rows include "1".

When the window is shifted by one in the X direction to perform detection of a next position after "1" has been detected in every row in the window, the just detected "1" might be read again.

So, once-read "1" is deleted from the memory to prevent one particulate from being counted twice.

After the scanning using the 6×X1 window is ended, another scan is carried out using a window having a size of 7×X1 while shifting the window one by one in the X direction. Since "1" has been deleted from the memory in the previous scanning, detection of S-shaped curves is carried out again, and the detected S-shaped curves are stored in the memory.

Then, scanning is carried out in like manner as that for the scanning with the 6×X1 window, and positions where all rows in the window include "1" are counted.

Thereby, the number of particulates each lying over six or more tracks and the number of particulates each lying over seven or more tracks are obtained, and the number of particulates each having a size equivalent to six tracks can be obtained from a difference between the numbers. The X1 is an integer value larger than a position deviation range of "1" due to uneven disc rotation or variations in signal detection. Therefore, even when a position error of "1" occurs in each track, it can be detected as "1" from the same particulate.

The conventional particulate determination method is carried out as described above. When particulates are adjacent to each other in the direction of the radius of the disc, 1s are continuously stored on the memory in a section corresponding to the adjacent particulates. Therefore, when scanning the memory using a scanning window, since 1s continue, a boundary of the adjacent particulates cannot be accurately detected. As a result, a problem occurs because several particulates adjacent to each other are undesirably detected as one particulate.

Further, in the above-mentioned conventional method, it is necessary to perform a plurality of scans while changing the size of the scanning window to determine the size of particulate. Further, since only one memory array is used, storage steps into the memory as many as the number of scannings are required, and therefore, a plurality of scans are required. As a result, particulate size determination and counting take much time.

Furthermore, in the conventional particulate determination method, when a plurality of particulates are adjacent to each other on the analysis disc, a number of S-shaped curves equal to the number of the particulates are detected in the track direction. However, in the radius direction, an end of a particulate abuts a beginning of another particulate. Therefore, after an end of a particulate is detected on a track, a beginning of another particulate is detected on a next track, and thereby 1s continue in the radius direction on the memory.

In this case, when the memory is scanned using a detection window, only a large particulate is detected although there are actually a plurality of particulates, and therefore, accurate counting cannot be carried out.

The present invention is made to solve the above-described problems and has for its object to provide a high-speed and high-precision particulate determination method which can determine the size of particulate by onetime scanning and, even when there are adjacent particulates, can correctly detect that these particulates are individual particulates.

Further, it is another object of the present invention to provide a particulate determination method which can accurately determine the size of particulate even when a plurality of particulates are adjacent to each other in the radius direction on the tracks.

BRIEF SUMMARY OF THE INVENTION

According to one embodiment of the invention, there is provided a particulate determination method for determining independence of a particulate as a measurement target according to a specific signal pattern that appears when a memory expressing a distribution of an electric signal is scanned along a predetermined scanning direction. The method includes: a data storage step of storing a plurality of different recognition conditions based on signal levels of the specific signal pattern, flags that are obtained when results of determinations according to the respective recognition conditions are true, and flags that are obtained when the results of determinations are false, into a plurality of memories which are provided correspondingly to the respective recognition conditions; and a particulate determination step of scanning arrays of the flags that are stored in the plural memories using scanning windows having the same predetermined size, and comparing rows of the flags in the same region on the memory expressing the distribution of the electric signal, among the arrays of the flags stored in the plural memories, thereby determining independence of the particulate. Independence of a particulate which is described in this specification indicates that, when a plurality of particulates are adjacent each other, the state is an assemblage of individual particulates. By detecting or determining independence of each particulate, the number of particulates can be counted when a plurality of particulates are adjacent to each other.

According to a second embodiment of the invention, the specific signal pattern is an S-shaped pattern (hereinafter referred to as an S-shaped curve) having a maximum value and a minimum value according to the size of the measurement target. The several recognition conditions include a condition that the size of the S-shaped curve is larger than a predetermined first threshold value, and several conditions adopting threshold values that are successively larger than the first threshold value.

According to a third embodiment of the invention, during the particulate determination step, it is determined as to whether the flags, which are obtained when the results of determinations in a plurality of scanning windows are true, exist continuously over a predetermined number of rows or more on the respective arrays of the flags. The independence of the particulate is determined by a combination of the results of determinations with the respective windows.

According to a fourth embodiment of the invention, there is provided a particulate determination method for determining independence of a particulate as a measurement target according to a specific signal pattern that appears when a memory expressing a distribution of an electric signal is scanned along a predetermined scanning direction. The method includes a data storage step of storing two different recognition conditions based on signal levels of the specific signal pattern. More specifically, flags that are obtained when results of determinations according to the respective recognition conditions are true and flags that are obtained when the results of determinations are false are stored into two memories which are provided corresponding to the respective recognition conditions. The method also includes a particulate determination step of scanning arrays of the flags that are stored in the two memories using two scanning windows having the same predetermined size, and comparing rows of the flags in the same region on the memory expressing the distribution of the electric signal, on the arrays of the flags stored in the two memories, thereby determining independence of the particulate.

According to a fifth embodiment of the invention, the specific signal pattern is an S-shaped curve having a maximum value and a minimum value according to the size of the measurement target. The two recognition conditions include a condition that the size of the S-shaped curve is larger than a predetermined first threshold value, and a condition that the size of the S-shaped curve is larger than a predetermined second threshold value that is larger than the first threshold value.

According to a sixth embodiment of the invention, during the particulate determination step, it is determined as to whether the flags, which are obtained when the results of determinations in the two scanning windows are true, exist continuously over a predetermined number of rows or more on the respective arrays of the flags. When a combination of the results of determinations using the respective scanning widows indicates that the result of determination using the first threshold value is true while the result of determination using the second threshold value is true, an individual particulate is recognized. When the combination indicates that the result of determination using the first threshold value is true while the result of determination using the second threshold value is false, a plurality of particulates is recognized. The number of the particulates being calculated from the number rows in which the flags, which are obtained when the results of determinations within the scanning windows are true, continuously exist.

According to a seventh embodiment of the invention there is provided a particulate determination method for determining independence of a particulate as a measurement target according to a specific signal pattern that appears when a memory expressing a distribution of an electric signal is scanned along a predetermined scanning direction. The method includes a data storage step of storing a predetermined recognition condition based on the shape of the specific signal pattern. More, specifically, a flag that is obtained when a result of determination according to the recognition condition is true, and a flag that is obtained when the result of determination is false, are stored into a memory. A particulate determination step includes scanning an array of the flags stored in the memory using a scanning window having a predetermined size, and determining independence of the particulate from rows of the flags obtained when the result of determination in the scanning window is true.

According to an eighth embodiment of the invention, the shape of the specific signal pattern is an S-shaped curve having a maximum value and a minimum value according to the size of the measurement target. The and the predetermined recognition condition is that a distance from a change start position to a change end position of the S-shaped curve in the track direction is larger than a predetermined value.

According to a ninth embodiment of the invention, the shape of the specific signal pattern is an S-shaped curve having a maximum value and a minimum value according to the size of the measurement target. The predetermined recognition condition is that a distance from a change start position to a change end position of the S-shaped curve in the track direction is larger than a predetermined value, and adjacent S-shaped curves have different lengths from a change start position to a change end position in the track direction.

According to a tenth embodiment of the invention, the particulate determination method includes a step of generating the signal pattern by irradiating an analysis medium into which the measurement target is injected, with a laser beam, and optically reading the analysis medium. The method also includes a step of providing a reference target having a predetermined size corresponding to the size of the measurement target in a predetermined region of the analysis medium, and setting a signal pattern obtained by reading the reference target before measurement, as a reference pattern. Moreover, the method includes a step of performing measurement on the basis of a result of comparison with the reference pattern, in the data storage step.

According to an eleventh embodiment of the invention the specific signal pattern and the reference pattern are S-shaped curves each having a maximum value and a minimum value according to the size of the measurement target. Measurement is carried out only when the result of a comparison with the reference pattern is that either the maximum value or the minimum value of the measurement target exists within the distribution range of the reference pattern.

According to a twelfth embodiment of the invention, the specific signal pattern and the reference pattern are S-shaped curves each having a maximum value and a minimum value according to the size of the measurement target. Measurement is carried out only when the result of comparison with the reference pattern is that both of the maximum value and the minimum value of the measurement target exist within the distribution range of the reference pattern.

According to a thirteenth embodiment of the invention, the particulate determination method is realized by a particulate determination device comprising an optical pickup which is provided movably with respect to the analysis disc, and comprises an optical system including a light source, an objective lens and the like. The particulate determination device also includes an actuator for driving the objective lens in a rotation axis direction and a radius direction of the analysis disc, and a photodetector for converting reflected light from the analysis disc into electricity. Moreover, the device includes: a spindle motor as a rotation driving means for the analysis disc; a servo control circuit for performing focus servo control, tracking servo control, and spindle servo control on the basis of a signal outputted from the optical pickup; a laser light reception unit (Photo Detector, hereinafter referred to as PD) for receiving a laser light which has been emitted from the optical pickup and has passed through the analysis disc, and converting the light into electricity; an S-shaped curve detection circuit for detecting an S-shaped curve on the basis of an electric signal outputted from the PD; a memory for holding the output of the S-shaped curve detection circuit; and a particulate recognition circuit for recognizing a particulate on the basis of data stored in the memory.

According to a fourteenth embodiment of the invention, there is provided a method for determining independence of a particulate as a measurement target which is injected into an analysis disc. The method includes: a step of storing, into a memory, an array of binary data comprising 0s and 1s, which is determined on the basis of the presence or absence of the particulate and the size of the particulate; and a step of determining the size of the particulate on the basis of the data array in a track direction and a radius direction of the analysis disc.

According to a fifteenth embodiment of the invention the data array in the track direction has a large number of 1s when an S-shaped curve, which is a particulate detection signal and has a maximum value and a minimum value, is large, and has a small number of 1s when the S-shaped curve is small.

According to a sixteenth embodiment of the invention, particulate, it is determined that there are a plurality of particulates when it is detected that 1s continue in the data array in the radius direction, and the number of 1s in the data array in the track direction decreases at some row.

According to a seventeenth embodiment of the invention, there is provided a method for determining independence of a particulate as a measurement target which is injected into an analysis disc. The method includes a step of writing a data array based on the size of an S-shaped curve which is a particulate detection signal and has a maximum value and a minimum value, on a memory, in a position next to a data array indicating the presence or absence of a particulate. It should be understood that, in this embodiment, According to continuous 1s do not exist in the encoded data array.

According to a nineteenth embodiment of the invention, there is provided a method for determining independence of a particulate as a measurement target which is injected into an analysis disc. When an S-shaped curve of a data array that is obtained when a particulate is detected is smaller than an S-shaped curve of a data array in a previous row, data are not stored on a memory. It should be understood that the data array comprises data indicating the presence or absence of a particulate, and data indicating the size of a particulate.

According to a twenty-first embodiment of the invention, the particulate determination method includes a step of writing "0" on the memory in a position next to "11" that is a data array indicating the presence or absence of a particulate. Also included is a step of writing, on the memory, a data array in which continuous 1s do not exist, which is determined on the basis of the size of an S-shaped curve that is a particulate detection signal and has a maximum value and a minimum value.

According to a twenty-second embodiment of the invention, the particulate determination method determines that there are a plurality of particulates when 1s continue in the data array in the radial direction, and the number of 1s in the data array in the track direction is the same in each row.

According to a twenty-third embodiment of the invention, the particulate determination method is realized by a particulate determination device comprising an optical pickup which is provided movably with respect to the analysis disc, and comprises an optical system including a light source, an objective lens and the like, an actuator for driving the objective lens in a rotation axis direction and a radius direction of the analysis disc, and a photodetector for converting a reflected light from the analysis disc into electricity. The particulate determination device also includes: electricity; a spindle motor as a rotation driving means for the analysis disc; a servo control circuit for performing focus servo control, tracking servo control, and spindle servo control on the basis of a signal outputted from the optical pickup; a PD for receiving a laser light which has been emitted from the optical pickup and has passed through the analysis disc, and converting the light into electricity; an S-shaped curve detection circuit for detecting an S-shaped curve on the basis of an electric signal outputted from the PD; a memory for holding an array of binary data which is processed on the basis of an output signal from the S-shaped curve detection circuit; and a particulate recognition circuit for recognizing a particulate on the basis of data stored in the memory.

EFFECTS OF THE INVENTION

According to one aspect of the present invention, there is provided a particulate determination method for determining independence of a particulate as a measurement target according to a specific signal pattern that appears when a memory expressing a distribution of an electric signal is scanned along a predetermined scanning direction, and the method includes: a data storage step of storing a plurality of different recognition conditions based on signal levels of the specific signal pattern, flags that are obtained when results of determinations according to the respective recognition conditions are true, and flags that are obtained when the results of determinations are false, into plural memories which are provided correspondingly to the respective recognition conditions; and a particulate determination step of scanning arrays of the flags that are stored in the plural memories using scanning windows having the same predetermined size, and comparing rows of the flags in the same region on the memory expressing the distribution of the electric signal, among the arrays of the flags stored in the plural memories, thereby determining independence of the particulate. Therefore, the number of particulates which are continuous in the direction of the radius of the disc can be counted without incorrectly recognizing the particulates, by comparing the states of the flags among the plural memory maps.

According to the present invention, in the particulate determination method, the specific signal pattern is an S-shaped pattern (hereinafter referred to as an S-shaped curve) having a maximum value and a minimum value according to the size of the measurement target; and the plural recognition conditions include a condition that the size of the S-shaped curve is larger than a predetermined first threshold value, and plural conditions adopting threshold values that are successively larger than the first threshold value. Therefore, the number of particulates which are continuous in the direction of the radius of the disc can be counted without wrongly recognizing the particulates, by setting appropriate threshold values.

According to the present invention, in the particulate determination method, in the particulate determination step, it is determined as to whether the flags, which are obtained when the results of determinations in the plural scanning windows are true, exist continuously over a predetermined number of rows or more on the respective arrays of the flags, and independence of the particulate is determined by a combination of the results of determinations with the respective windows. Therefore, the number of particulates which are continuous in the direction of the radius of a disc can be counted without wrongly recognizing the particulates, according to the results of determinations using the scanning windows.

According to another aspect of the present invention, there is provided a particulate determination method for determining independence of a particulate as a measurement target according to a specific signal pattern that appears when a memory expressing a distribution of an electric signal is scanned along a predetermined scanning direction, and the method includes: a data storage step of storing two different recognition conditions based on signal levels of the specific signal pattern, flags that are obtained when results of determinations according to the respective recognition conditions are true, and flags that are obtained when the results of determinations are false, into two memories which are provided correspondingly to the respective recognition conditions; and a particulate determination step of scanning arrays of the flags that are stored in the two memories using two scanning windows having the same predetermined size, and comparing rows of the flags in the same region on the memory expressing the distribution of the electric signal, on the arrays of the flags stored in the two memories, thereby determining independence of the particulate. Therefore, the number of particulates which are continuous in the direction of the radius of a disc can be counted without wrongly recognizing the particulates, by comparing the states of the flags between the two memory maps corresponding to the threshold values of different levels.

According to the present invention, in the particulate determination method, the specific signal pattern is an S-shaped curve having a maximum value and a minimum value according to the size of the measurement target; and the two recognition conditions include a condition that the size of the S-shaped curve is larger than a predetermined first threshold value, and a condition that the size of the S-shaped curve is larger than a predetermined second threshold value that is larger than the first threshold value. Therefore, the number of particulates which are continuous in the direction of the radius of a disc can be counted without wrongly recognizing the particulates, by setting appropriate threshold values.

According to the present invention, in the particulate determination method, in the particulate determination step, it is determined as to whether the flags, which are obtained when the results of determinations in the two scanning windows are true, exist continuously over a predetermined number of rows or more on the respective arrays of the flags; when a combination of the results of determinations using the respective scanning widows indicates that the result of determination using the first threshold value is true while the result of determination using the second threshold value is true, an individual particulate is recognized; and when the combination indicates that the result of determination using the first threshold value is true while the result of determination using the second threshold value is false, plural particulates are recognized, the number of the particulates being calculated from the number rows in which the flags, which are obtained when the results of determinations within the scanning windows are true, continuously exist. Therefore, the number of particulates which are continuous in the direction of the radius of a disc can be counted without wrongly recognizing the particulates, according to the results of determinations using the scanning windows.

According to another aspect of the present invention, there is provided a particulate determination method for determining independence of a particulate as a measurement target according to a specific signal pattern that appears when a memory expressing a distribution of an electric signal is scanned along a predetermined scanning direction, and the method includes: a data storage step of storing a predetermined recognition condition based on the shape of the specific signal pattern, a flag that is obtained when a result of determination according to the recognition condition is true, and a flag that is obtained when the result of determination is false, into a memory; and a particulate determination step of scanning an array of the flags stored in the memory using a scanning window having a predetermined size, and determining independence of the particulate from rows of the flags obtained when the result of determination in the scanning window is true. Since the particulate recognition condition corresponding to the size of a particulate to be detected has previously been set, even when plural particulates adjoin to each other in a direction perpendicular to the scanning direction, the target particulate is not misidentified, whereby the number of particulates which are continuous in the direction of the radius of a disc can be counted without wrongly recognizing the particulates.

According to the present invention, in the particulate determination method, the shape of the specific signal pattern is an S-shaped curve having a maximum value and a minimum value according to the size of the measurement target; and the predetermined recognition condition is that a distance from a change start position to a change end position of the S-shaped curve in the track direction is larger than a predetermined value. Therefore, the number of particulates which are continuous in the direction of the radius of a disc can be counted without wrongly recognizing the particulates, by setting appropriate threshold values.

According to the present invention, in the particulate determination method, the shape of the specific signal pattern is an S-shaped curve having a maximum value and a minimum value according to the size of the measurement target; and the predetermined recognition condition is that a distance from a change start position to a change end position of the S-shaped curve in the track direction is larger than a predetermined value, and adjacent S-shaped curves have different lengths from a change start position to a change end position in the track direction. Therefore, the number of particulates which are continuous in the direction of the radius of a disc can be counted without wrongly recognizing the particulates, by setting appropriate threshold values.

According to the present invention, the particulate determination method includes: a step of generating the signal pattern by irradiating an analysis medium into which the measurement target is injected, with a laser beam, and optically reading the analysis medium; a step of providing a reference target having a predetermined size corresponding to the size of the measurement target in a predetermined region of the analysis medium, and setting a signal pattern obtained by reading the reference target before measurement, as a reference pattern; and a step of performing measurement on the basis of a result of comparison with the reference pattern, in the data storage step. Therefore, only the particulates having the size equal to the size of the measurement target can be counted by comparing the reference value of the detection signal before it is inputted, with the detection signal obtained when the actual particulate recognition is carried out. Even when plural particulates adjoin to each other in a direction perpendicular to the scanning direction, the target particulate is not misidentified, whereby the number of particulates which are continuous in the direction of the radius of a disc can be counted without wrongly recognizing the particulates.

According to the present invention, in the particulate determination method, the specific signal pattern and the reference pattern are S-shaped curves each having a maximum value and a minimum value according to the size of the measurement target; and measurement is carried out only when the result of comparison with the reference pattern is that either the maximum value or the minimum value of the measurement target exists within the distribution range of the reference pattern. Therefore, the number of particulates which are continuous in the direction of the radius of a disc can be counted without wrongly recognizing the particulates, by setting appropriate threshold values.

According to the present invention, in the particulate determination method, the specific signal pattern and the reference pattern are S-shaped curves each having a maximum value and a minimum value according to the size of the measurement target; and measurement is carried out only when the result of comparison with the reference pattern is that both of the maximum value and the minimum value of the measurement target exist within the distribution range of the reference pattern. Therefore, the number of particulates which are continuous in the direction of the radius of a disc can be counted without wrongly recognizing the particulates, by setting appropriate threshold values.

According to another aspect of the present invention, there is provided a method for determining independence of a particulate as a measurement target which is injected into an analysis disc, and the method includes: a step of storing, into a memory, an array of binary data comprising 0s and 1s, which is determined on the basis of presence/absence of the particulate and the size of the particulate; and a step of determining the size of the particulate on the basis of the data array in a track direction and a radius direction of the analysis disc. Therefore, even when plural particulates adjoin each other in the radius direction on the tracks, the sizes of the particulates can be accurately determined to count the particulates.

According to another aspect of the present invention, there is provided a method for determining independence of a particulate as a measurement target which is injected into an analysis disc, and this method includes: a step of writing "0" on the memory in a position next to "11" that is a data array indicating presence/absence of a particulate; and a step of writing, on the memory, a data array in which continuous 1s do not exist, which is determined on the basis of the size of an S-shaped curve that is a particulate detection signal and has a maximum value and a minimum value. Therefore, in the step of detecting presence/absence of particulate, only the arrays of "11" should be detected, without the necessity of observing the number of 1s in the respective rows in the window. Therefore, detection of particulates can be carried out without complicated operation of the detection window. Further, in the step of determining the particulate size, even when plural particulates on the tracks adjoin to each other in the radius direction, the size of each particulate can be accurately determined to count the particulates. Furthermore, when the data array indicating the size of the S-shaped curve is composed of five or more digits, the number of handleable data increases, whereby finer division is possible, and it is advantageous when fine division is required.

According to another aspect of the present invention, there is provided a method for determining independence of a particulate as a measurement target which is injected into an analysis disc, wherein, when an S-shaped curve of a data array that is obtained when a particulate is detected is smaller than an S-shaped curve of a data array in a previous row, data are not stored on a memory. Therefore, even when plural particulates on the tracks adjoin to each other in the radius direction, the size of each particulate can be accurately determined to count the particulates.

BRIEF DESCRIPTION OF THE DRAWINGS

FIG. 5(a) is a diagram of an example of a memory array according to the first and second embodiments.

FIG. 5(b) is a diagram of an example of a memory array according to the first and second embodiments.

FIG. 5(c) is a diagram of an example of a memory array according to the first and second embodiments.

FIG. 5(d) is a diagram of an example of a memory array according to the first and second embodiments.

FIG. 6(a) is a diagram illustrating the state of a scanning window employed in the particulate determination method according to the first embodiment.

FIG. 6(b) is a diagram illustrating the state of a scanning window employed in the particulate determination method according to the first embodiment.

FIG. 6(c) is a diagram illustrating the state of a scanning window employed in the particulate determination method according to the first embodiment.

FIG. 6(d) is a diagram illustrating the state of a scanning window employed in the particulate determination method according to the first embodiment.

FIG. 11(a) is a diagram illustrating the state of a scanning window employed in the particulate determination method according to the second embodiment.

FIG. 11(b) is a diagram illustrating the state of a scanning window employed in the particulate determination method according to the second embodiment.

FIG. 11(c) is a diagram illustrating the state of a scanning window employed in the particulate determination method according to the second embodiment.

FIG. 11(d) is a diagram illustrating the state of a scanning window employed in the particulate determination method according to the second embodiment.

FIG. 15 is a diagram for explaining an example of a memory array in the particulate determination method according to the third embodiment.

FIG. 23(b) is a diagram illustrating a data array stored in a memory in the particulate determination method according to the sixth embodiment.

FIG. 23(b) is a diagram illustrating a data array stored in a memory in the particulate determination method according to the seventh embodiment.

DETAILED DESCRIPTION OF THE PREFERRED EMBODIMENTS

Hereinafter, embodiments of particulate determination methods according to the present invention will be described with reference to the drawings.

Embodiment 1

Figure 1:
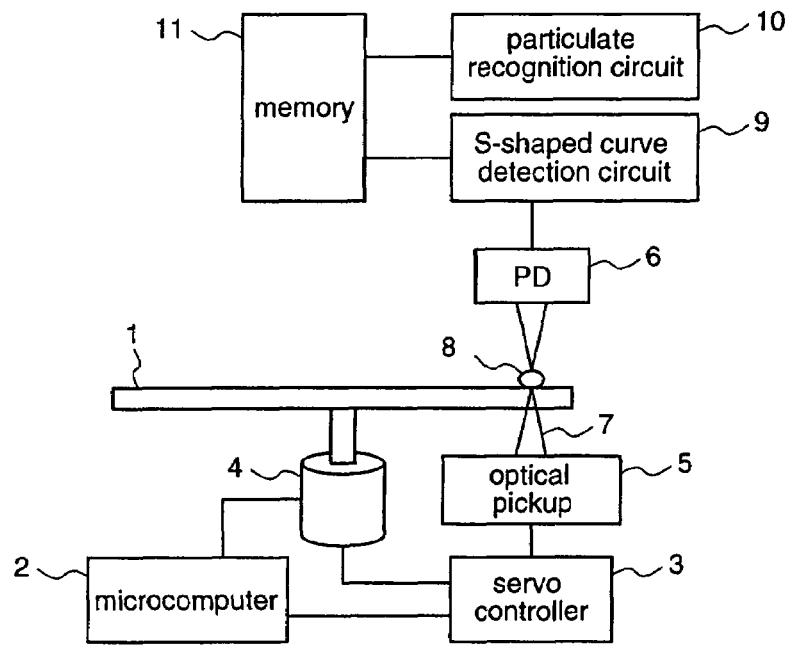
FIG. 1 is a block diagram illustrating an analysis device using a particulate determination method according to a first embodiment of the present invention.

FIG. 1 is a block diagram illustrating an analysis device employing a particulate determination method according to a first embodiment of the present invention. Hereinafter, the fundamental operation of the device will be described.

When an analysis disc 1 on which particulates as an analysis target 8 are placed is mounted on an analysis device, rotation control (CAV control) for a spindle motor 4 is carried out by a servo control circuit 3 connected to a microcomputer 2.

Next, the analysis disc 1 is irradiated with a laser beam 7 emitted from an optical pickup 5. The servo control circuit 3 performs focus servo, tracking servo, and traverse control to trace tracks formed of pits or grooves on the basis of a reproduced output signal from the optical pickup 5, and simultaneously, detects address information recorded on the tracks of the analysis disc 1, and controls rotation of the spindle motor 4 so as to make the linear velocity constant (CLV control).

Thus, tracing, which is an operation to make the optical pickup 5 follow the tracks on the disc 1, is carried out, and reflected light or transmitted light from the analysis disc 1 at this time is detected by a PD (photodetector) 6 (FIG. 1 shows the case of transmitted light), whereby scanning for analyzing the analysis target 8 can be carried out on the basis of the detected signal.

Next, a description will be given of a method for detecting a single-body particulate from the signal detected by the PD 6 during particulate recognition at scanning (hereinafter referred to as PD detection signal), using an S-shaped curve detection circuit 9 and a particulate recognition circuit 10, with reference to FIG. 2, which method is a feature of the present invention.

Figure 2A:
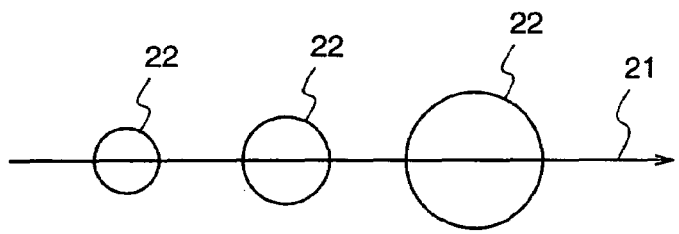
FIG. 2(a) is a diagram illustrating examples of particulates and S-shaped curves obtained in accordance with the first embodiment of the invention.

FIG. 2(a) shows an example wherein the centers of three particulates 22 having different sizes are positioned on the same track 21.

Figure 2B:
FIG. 2(b) is a diagram illustrating examples of particulates and S-shaped curves obtained in accordance with the first embodiment of the invention.

FIG. 2(b) shows a waveform of a PD detection signal which is obtained when the track 21 is traced in the example of FIG. 2(a).

As shown in FIG. 2(b), the waveform is constant when no particulate exists, while it curves in an S shape when a particulate exists. In this first embodiment, the amplitude of the S-shaped curve is proportional to the size of the particulate.

The S-shaped curve detection circuit 9 detects the change in the PD detection signal on the basis of a predetermined recognition condition, and writes "0" as a flag on the memory when no S-shaped curve is detected, while writes "1" as a flag on the memory 11 when an S-shaped curve is detected.

The predetermined recognition condition is as follows. For example, using the amplitude of the PD detection signal and a predetermined threshold value, it is determined that no S-shaped curve is detected when the amplitude is smaller than the predetermined threshold value, while it is determined that an S-shaped curve is detected when the amplitude is larger than the threshold value.

As described above, the S-shaped curve detection circuit 9 reflects the presence or absence of an S-shaped curve in the PD detection signal onto the memory. The data in the memory 11 thus generated form a two-dimensional memory array in which one direction indicates the track direction of the disc while the other direction indicates the radial direction of the disc.

Further, in this first embodiment, a plurality of recognition conditions are used for onetime scanning to constitute a plurality of memory arrays to which the results of determinations according to the respective recognition conditions are reflected.

In this first embodiment, it is assumed that there are three kinds of particulates A, B, and C having different sizes (A<B<C), and four threshold values a1, a2, a3, and a4 (a1<a2<a3<a4) are used as the above-mentioned predetermined recognition conditions.

Hereinafter, a description will be given of a method for setting the recognition conditions according to the first embodiment, i.e., the respective threshold values.

As shown in FIG. 2(a), a track that passes through the centers of the three particulates A, B, and C will be considered. FIG. 2(b) is a graph illustrating the relationship between the S-shaped curves of the particulates A, B, and C that are generated on the track, and the four threshold values a1, a2, a3, and a4.

As shown in FIG. 2(b), the threshold values a1~a4 are set so that the S-shaped curves detected at the respective threshold values have different sizes.

Figures 3, 4:
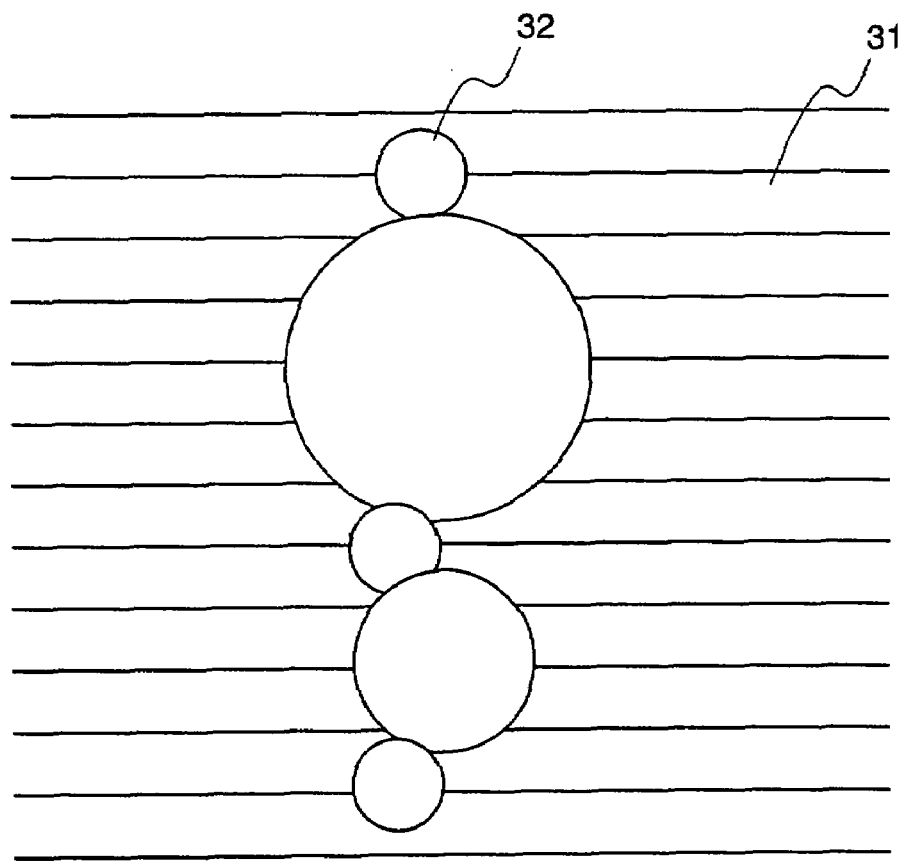
FIG. 3 is a diagram illustrating a table expressing the relationship between the types of the particulates and threshold values.
FIG. 4 is a diagram illustrating examples of particulates which are arranged in the radial direction a disc according to the first and second embodiments.

Hereinafter, memory arrays A1~A4 which are constituted corresponding to the respective threshold values will be described in detail. FIG. 3 shows a table expressing the relationship between the different types of particulates and the threshold values according to the first embodiment. In FIG. 3, each numerical value indicates the number of rows which include 1s that appear continuously in the radial direction on the memory array, when the respective particulates A, B, and C having different sizes exist.

For example, as for the particulate C, 1s appear continuously over five rows in the memory array A1 corresponding to the threshold value a1, over three rows in the memory array A2 corresponding to the threshold value a2, and in only one row in the memory array A3 corresponding to the threshold value a3. No 1 appears in the memory array A4 corresponding to the largest threshold value a4. In this way, the number of 1s that appear on the memory array decreases with an increase in the threshold value.

When the particulates shown in FIG. 3 are observed according to the types, the level of the threshold value at which no 1 appears becomes larger according to the size of the particulate. For example, as for the smallest particulate A, the frequency of 1 becomes zero with respect to the threshold values equal to or larger than the threshold value a2. However, as for the largest particulate C, the frequency of 1 becomes zero with respect to the threshold value a4 alone.

The table shown in FIG. 3 is used for determining the size of particulate, which will be described later. Accordingly, this table should be prepared in advance, and it is necessary to uniquely determine the type of particulate from the smallest threshold value at which no 1 appears, using this table. As for the respective threshold values, appropriate values are set so as to uniquely determine all types of particulates.

The memory arrays A1~A4 are generated using the threshold values a1~a4 that are set as described above.

Next, with reference to FIG. 5, a description will be given of a method for recognizing a plurality of particulates that continuously exist in the radial direction of the analysis disc as shown in FIG. 4, as individual particulates, from the generated memory arrays A1~A4.

FIGS. 5(a)-5(d) show the states of the respective memory arrays in an area including the particulates shown in FIG. 4. Particularly, FIG. 5(a) shows the memory array A1 corresponding to the threshold a1, FIG. 5(b) shows the memory array A2 corresponding to the threshold value a2, FIG. 5(c) shows the memory array A3 corresponding to the threshold value a3, and FIG. 5(d) shows the memory array A4 corresponding to the threshold value a4.

Scanning is carried out to search the array of FIG. 5(a) for a position where the scanning point becomes 1 while sifting the scanning point one by one in the row direction up to the right end, with the upper left end of FIG. 5(a) as a base point. When the scanning to the right end is completed, scanning is carried out with the left end of the next row as a base point, while shifting the scanning point one by one in the row direction up to the right end. This scanning is repeatedly carried out.

When it is detected that a 1 exists in the scanning point, a particulate recognition process to be described later is carried out. After the particulate recognition process is completed, scanning is continued with the scanning point being shifted by one.

Hereinafter, the particulate recognition process will be described with reference to FIGS. 6(a)-6(d).

FIGS. 6(a)-6(d) are diagrams illustrating the states in the scanning window, for explaining the particulate size determination process. In FIGS. 6(a)-6(d), "1" indicates that there is at least one 1 in the corresponding row in the scanning window, and "0" indicates that all of the scanning points in the corresponding row in the scanning window are 0. That is, 1s and 0s shown in FIGS. 6(a)-6(d) are the results of OR calculated in the row direction with respect to the respective rows in the scanning window. The state of the scanning window 41 shown in FIGS. 5(a)-5(b) is shown in FIG. 6(a). The state in the scanning window 41 that will appear in the following description will be expressed as described above.

Figure 7:
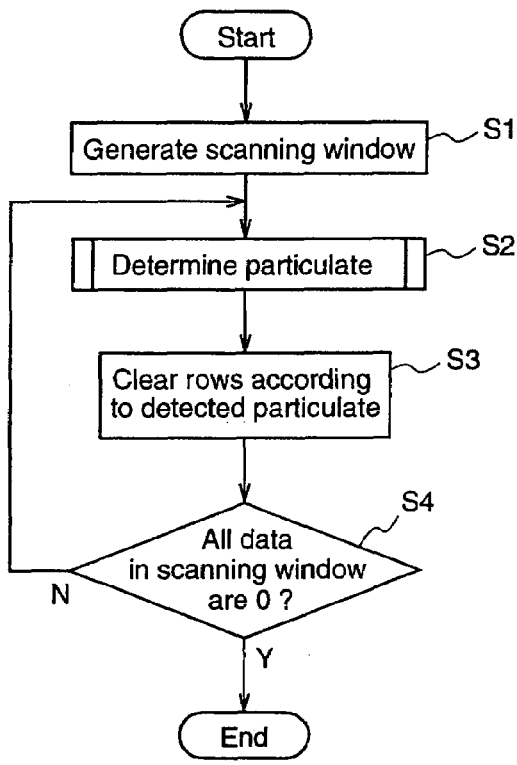
FIG. 7 is a flowchart illustrating a particulate recognition process in the particulate determination method according to the first embodiment.

FIG. 7 is a flowchart of the particulate recognition process according to the first embodiment.

Initially, in step S1, a scanning window 41, the range of which is extended as far as 1s continue in the row direction from the scanning point, is generated. This scanning window has a predetermined width in the column direction. The predetermined width is a width in which all of 1s generated with respect to one particulate remain in the scanning window, and it is previously obtained by actual measurement or the like.

Next, in step S2, the particulate size is obtained by performing a particulate size determination process to be described later.

In step S3, with reference to the table shown in FIG. 3, the rows in the scanning window 41 in each memory array are successively cleared from the top, by the number of continuous 1s corresponding to the obtained particulate size (all of the data in one row are set to 0).

In step S4, it is judged whether, on the memory array A1, all of the data in the scanning window 41 is 0 or not. When the result of judgement is true, i.e., when all of the data is 0, the particulate recognition process is ended. On the other hand, when the result of the judgement is false, i.e., 1 still remains in any row, the operation goes back to step S1 to continue the particulate recognition process.

FIG. 6(b) shows the state of the scanning window and the counting condition at the point where the process reaches step S4 for the first time. In step S2, the particulate C is detected. In step S3, the rows where 1s exist are cleared over 5 rows in the memory array A1, 3 rows in the memory array A2, and 1 row in the memory array A3. Since, at this point, 1s still remain in the scanning window 41, the process returns to step S2 to continue the particulate recognition process.

FIG. 6(c) shows the state of the scanning window and the counting condition at the point where the process reaches step S4 for the second time. In step S2, the particulate B is detected. In step S3, the rows where 1s exist are cleared over 3 rows in the memory array A1, and 1 row in the memory array A2. Since, at this point, 1s still remain in the scanning window 41, the process returns to step S2 to continue the particulate recognition process.

Thereafter, the processes from step S2 to step S4 are repeated similarly. In step S2, the particulate A is detected in the third time, the fourth time, and the fifth time, and every time the particulate A is detected, only one row where 1s exist on the memory array A1 is cleared in step S3. FIG. 6(d) shows the state of the scanning window and the counting condition at the point of time when the process reaches step S4 in the fifth time. At this point, all of the data in the scanning window 41 is 0, and therefore, the particulate recognition process is completed.

Next, a description will be given of the particulate size determination process to be carried out in step S2 described above.

Figure 8:
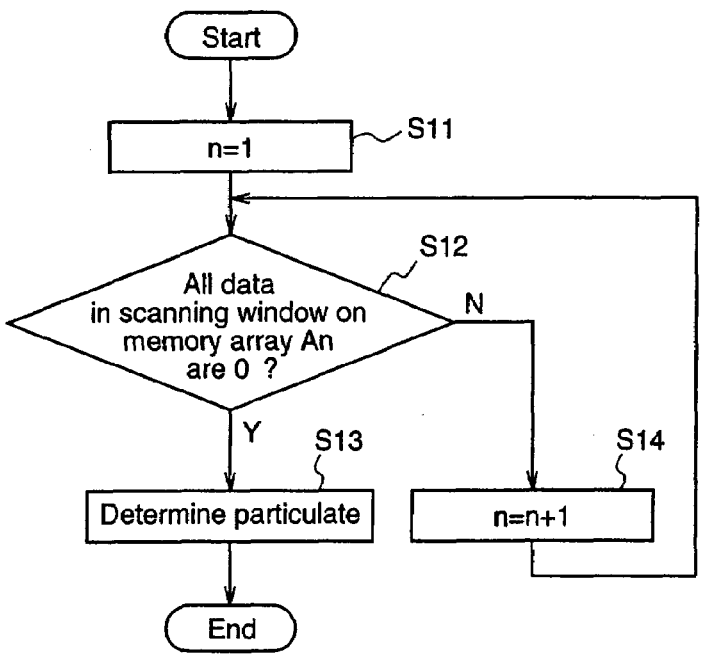
FIG. 8 is a flowchart illustrating a particulate size determination process in the particulate determination method according to the first embodiment.

FIG. 8 is a flowchart for explaining the particulate size determination process according to the first embodiment.

In step S11, a variable n is initialized to 1. This variable n is employed to express repetition of the process in the description of the flowchart.

In step S12, it is judged whether all of the data in the scanning window 41 is 0 or not on the memory array An.

When the result of determination in step S12 is true, i.e., when all of the data in the window is 0, the process goes to step S13. In step S13, with reference to the table shown in FIG. 3, the particulate type is determined from the value of n. For example, when n=3, it is determined as the particulate B in which the minimum threshold value at which no 1 appears is the threshold value a3.

On the other hand, when the result of determination in step S12 is false, i.e., when 1 still remains in any row, the process goes to step S14, and the value of n is incremented by one. Then, the process returns to step S12 to continue.

By performing the above-mentioned scanning over the whole areas of the memory arrays, counting of particulates is carried out while determining the sizes of particulates.

As described above, according to the first embodiment, the S-shaped curve detection circuit 9 constitutes plural memory arrays corresponding to different recognition conditions, and detects S-shaped curves using the different recognition conditions (threshold values). Then, the particulate recognition circuit 10 analyzes a combination of appearance patterns of 1s on the memory maps corresponding to the respective recognition conditions. Thereby, the number of particulates can be counted without wrongly recognizing plural particulates that are continuous in the radial direction of the disc.

Further, in this first embodiment, when the width of the S-shaped curve increases in proportion to the size of the particulate, a similar particulate size determination method can be applied by setting the threshold values not in the amplitude direction but in the time-base direction.

Figures 9, 10:
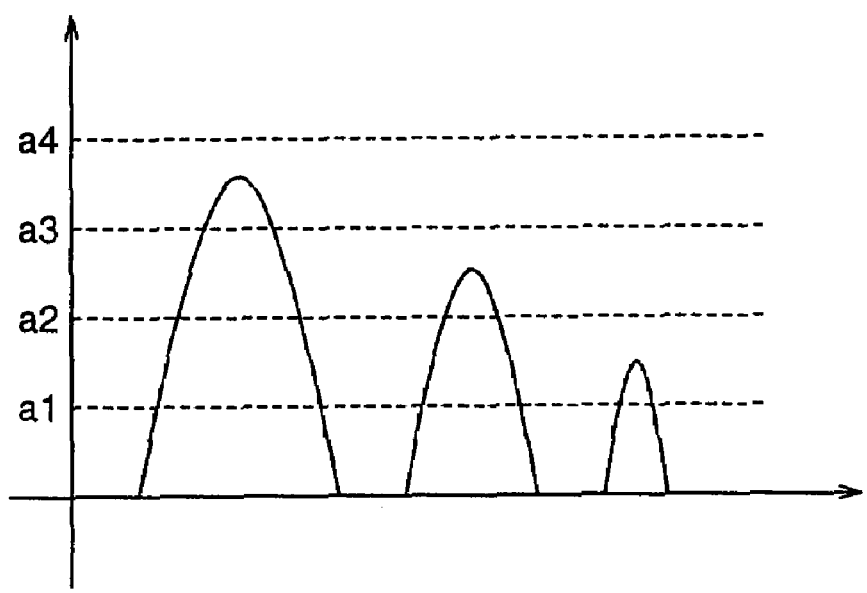
FIG. 9 is a diagram of an example of a convex signal in the particulate determination method according to the first embodiment.
FIG. 10 is a diagram illustrating a table expressing the relationship between the types of the particulates and threshold values according to the second embodiment.
Figure 13:
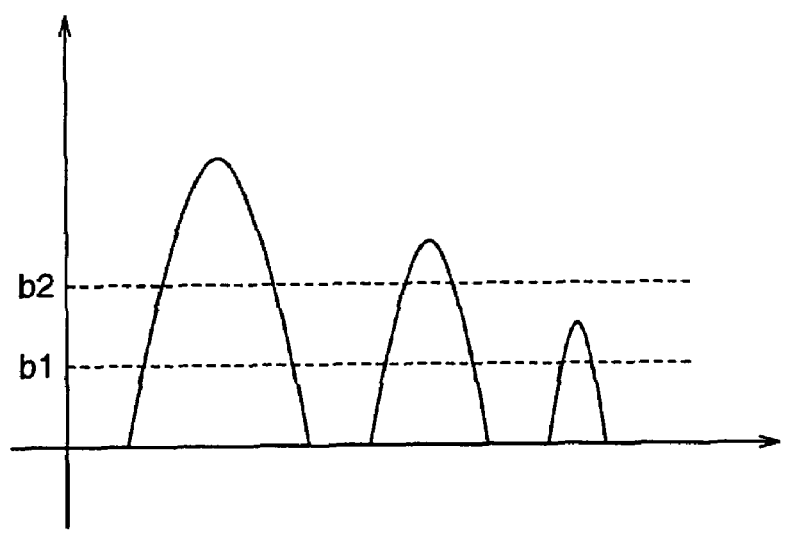
FIG. 13 is a diagram of an example of a convex signal in the particulate determination method according to the second embodiment.

Furthermore, the PD detection signal according to the first embodiment may be a convex signal as shown in FIG. 13, instead of the S-shaped curve signal shown in FIG. 2(b). Also in this case, a similar particulate size determination and counting can be carried out by constituting the memory arrays with the threshold values being set like a1, a2, a3, and a4 as shown in FIG. 9.

Embodiment 2

Next, a particulate determination method according to a second embodiment of the present invention will be described. A block diagram of a device to which the second embodiment is applied is identical to that shown in FIG. 1 according to the first embodiment.

Hereinafter, a characteristic operation of the particulate determination method according to the second embodiment will be described.

A description will be given of a threshold value b1 and a threshold value b2 (b1<b2) corresponding to the amplitude of an S-shaped curve, and a memory array B1 and a memory array B2 which are generated using the respective threshold values.

FIG. 10 shows the number of 1s that appear continuously in the radial direction on each memory array, when the particulates D, E, and F having different sizes exist.

When FIG. 10 is referred to for each particulate, the number of rows in which is appear continuously on the memory array B2 corresponding to the threshold value b2 increases with an increase in the particulate size. For example, as for the smallest particulate D, the number of occurrences of 1s corresponding to the threshold value b2 is 0. As for the largest particulate F, the number of occurrences of 1s 3.

The table shown in FIG. 10 will be used for particulate size determination to be described later. Accordingly, this table should be prepared in advance, and the particulate type should be uniquely determined from the number of rows where 1s continuously appear with respect to the threshold value b2, using this table. The respective threshold values are set to appropriate values so that all types of particulates can be uniquely determined.

The memory arrays B1 and B2 are generated using the threshold values b1 and b2 which are set as described above. Next, a description will be given of a method for recognizing the particulates which exist continuously in the radial direction of the analysis disc as shown in FIG. 4, as individual particulates, from the generated memory arrays B1 and B2, with reference to FIGS. 5(a)-5(d)

FIGS. 5(a)-5(d) show the states of the respective memory arrays in the area including the particulates shown in FIG. 4. Particularly, FIG. 5(a) shows the memory array B1 corresponding to the threshold value b1, and FIG. 5(b) shows the memory array B2 corresponding to the threshold value b2.

The memory array B1 is searched for a position where the scanning point becomes 1, with the upper left of FIG. 5(a) as a base point, while shifting the scanning point one by one in the row direction up to the right end. When scanning up to the right end is completed, scanning is carried out with the left end of the next row as a base point, while shifting the scanning point one by one in the row direction up to the right end of the row. This scanning is repeatedly carried out.

When it is detected that 1 exists at a scanning point, a particulate recognition process to be described later is carried out. After the particulate recognition process, the scanning point is shifted by one to continue scanning.

Hereinafter, the particulate recognition process will be described with reference to FIGS. 11(a)-11(d). FIGS. 11(a)-11(d) show the states in the scanning window 41, for explaining a particulate size determination process. Since the method of expressing the states in the scanning window shown in FIGS. 11(a)-11(d) is identical to that described with respect to FIGS. 6(a)-6(b) according to the first embodiment, repeated description is not necessary.

Figure 12:
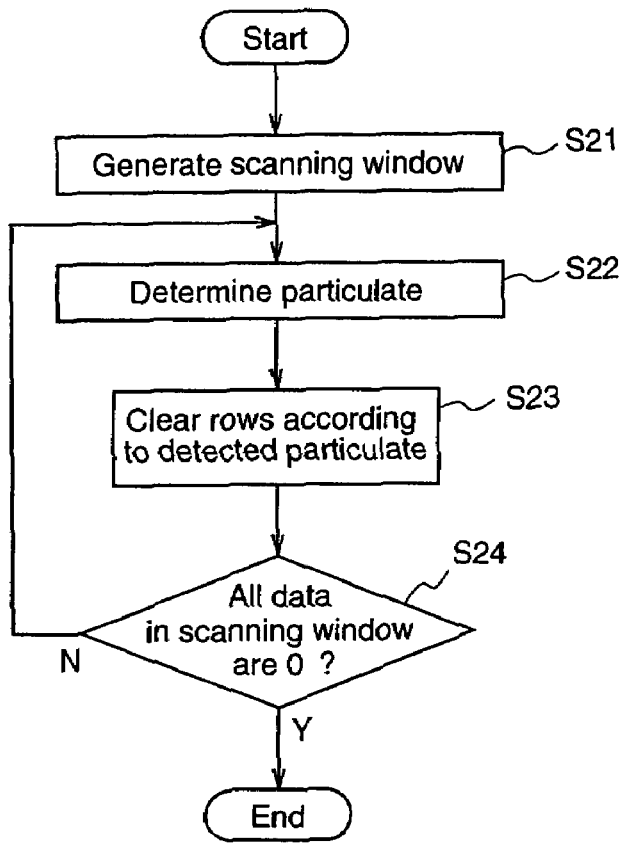
FIG. 12 is a flowchart illustrating a particulate recognition process in the particulate determination method according to the second embodiment.

FIG. 12 is a flowchart of the particulate recognition process according to the second embodiment.

When the process is started, in step S21, a scanning window 41, the range of which is extended as far as 1s continue in the row direction from the scanning point, is generated. The scanning window 41 has a predetermined width in the column direction. The predetermined width should be previously obtained so that all of 1s generated for one particulate are contained in the scanning window 41.

Next, in step S22, on the memory array B2, the respective rows in the scanning window 41 are scanned from the top, and the number of rows in which 1s continue is counted from a row in which 1 is detected for the first time, and the size of the particulate is determined with reference to the table shown in FIG. 10. For example, when the state in the scanning window 41 is as shown in FIG. 11(a), continuous 1s exist in the three rows, i.e., from the third row to the fifth row, on the memory array B2, and therefore, it is determined as the particulate F from the table shown in FIG. 10.

Next, in step S23, with reference to the table shown in FIG. 10, the rows in the scanning window 41 of each memory array are cleared successively from the top, by the number of continuous 1s corresponding to the size of the obtained particulate (all of the data in one row are set to 0).

In step S24, it is judged whether all of the data in the scanning window 41 is 0 or not on the memory array B1. When the result of the judgment is true, i.e., when all of the data is 0, the particulate recognition process is ended. On the other hand, when the result of the judgment is false, i.e., when 1 still remains in any row, the process returns to step S21, and the particulate recognition process 1s continued.

FIG. 11(b) shows the state in the scanning window 41 and the condition of counting at the point of time when the process reaches step S24 for the first time. The particulate F has been detected in step S22, and five rows where 1s exist have been cleared in the memory array B1 while three rows where 1s exist have been cleared in the memory array B2, in step S23. At this time, since 1s still remain in the scanning window 41, the process returns to step S22 to continue the particulate recognition process.

FIG. 11(c) shows the state in the scanning window 41 and the counting condition at the point of time when the process reaches step S24 for the second time. The particulate E has been detected in step S22, and three rows where 1s exist have been cleared in the memory array B1 while one row where 1 exists has been cleared in the memory array B2, in step S23. At this time, since 1s still remain in the scanning window 41, the process returns to step S22, and the particulate recognition process is continued.

Hereinafter, the processes of steps S22 to S24 are continued similarly. In step S22, the particulate D is detected in the third time, the fourth time, and the fifth time, and every time the particulate D is detected, one row where 1 exists is cleared on the memory array B1 in the next step S23. FIG. 11(d) shows the state of the scanning window 41 and the counting condition at the point of time when the process reaches step S24 for the fifth time. At this time, all of the data in the scanning window 41 is 0, and therefore, the particulate recognition process is ended.

By performing the above-mentioned scanning over the whole areas of the memory arrays, counting of particulates is carried out while determining the sizes of the particulates.

As described above, in the second embodiment, there are provided two patterns of memory arrays, i.e., the memory array B1 corresponding to the threshold value b1 and the memory array B2 corresponding to the threshold value b2, and a combination of patterns of occurrences of 1 on the respective memory arrays is analyzed, whereby the sizes of particulates can be recognized and the number of the particulates can be counted without wrongly recognizing the plural particulates that continuously exist in the radial direction of the disc.

When the width of the S-shaped curve increases in proportion to the particulate size, a similar particulate size determination method can be applied by setting the threshold values not in the amplitude direction but in the time axis direction.

Further, instead of the S-shaped curve signal shown in FIG. 2(b), a convex signal as shown in FIG. 13 may be employed as a PD detection signal. Also in this case, similar particulate size determination and counting can be carried out by constituting the memory arrays with the threshold values being set like b1 and b2 shown in FIG. 13.

Embodiment 3

Figure 14A:
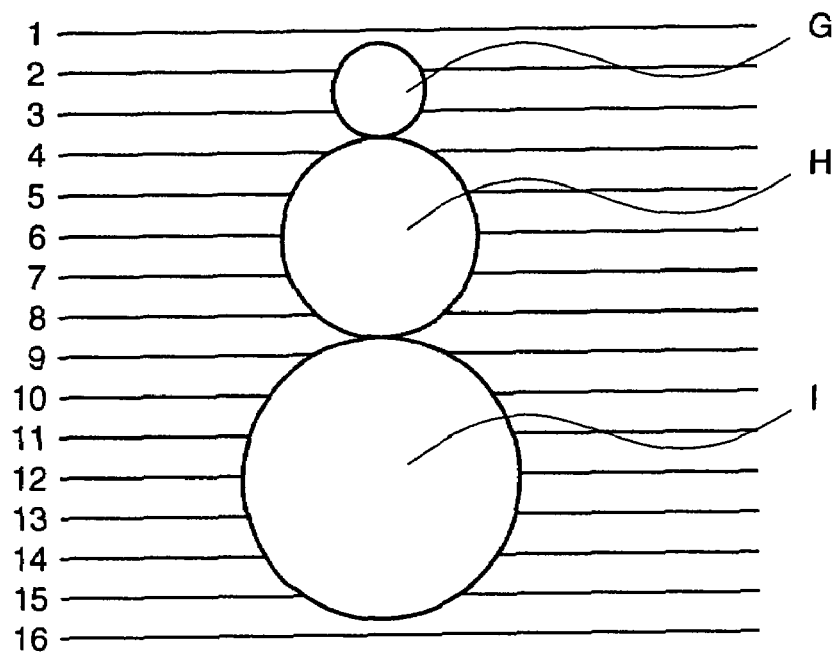
FIG. 14(a) is a diagram illustrating arrangement of particulates on an optical disc in a particulate determination method according to a third embodiment of the present invention.
Figure 14B:
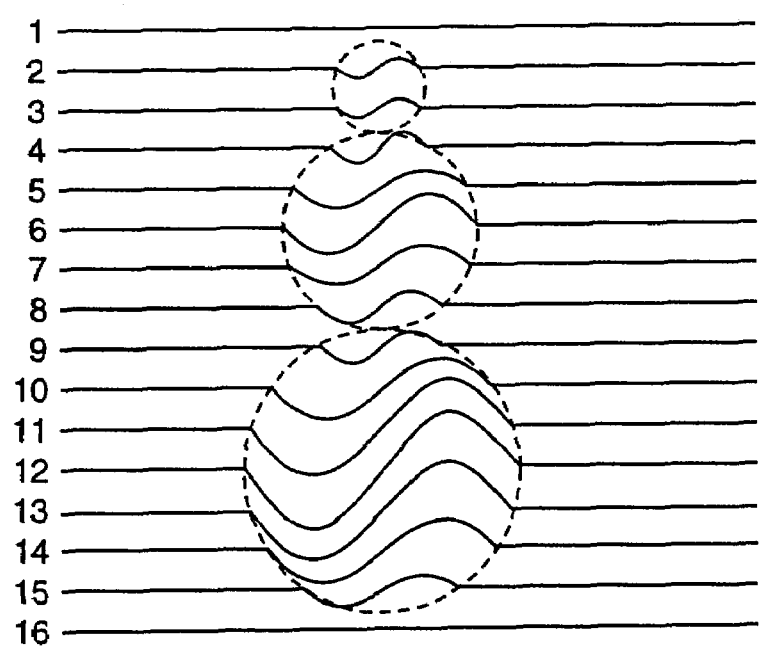
FIG. 14(b) is a diagram illustrating examples of signal patterns which are obtained from the arrangement of the particulates on the optical disc in the particulate determination method according to the third embodiment.

Next, a particulate determination method according to a third embodiment of the present invention will be described. FIG. 14(a) is a diagram illustrating a layout of particulates on an optical disc in the particulate determination method according to the third embodiment of the present invention. FIG. 14(b) shows signal patterns corresponding to the particulates on the optical disc shown in FIG. 14(a). Further, FIG. 15 shows a memory array indicating a result of determination that is performed on FIG. 14(b) according to a particulate recognition condition.

A block diagram of a device to which the particulate determination method according to the third embodiment is applied is identical to the construction shown in FIG. 1 according to the first embodiment.

Hereinafter, characteristic processes in the particulate determination method according to the third embodiment will be described.

It is assumed that, as shown in FIG. 14(a), a particulate G, a particulate H, and a particulate I are placed over tracks 1 to 16 on the optical disc. That is, the particulate G is placed on the tracks 2 and 3, the particulate H is placed on the tracks 4 to 8, and the particulate I is placed on the tracks 9 to 15.

In this case, signal patterns generated along the respective tracks S-shaped patterns shown in FIG. 14(b) (hereinafter referred to as S-shaped curves). Each S-shaped curve appears within a range between two intersection points of each track and the outermost circumference of each particulate.

Figure 16:
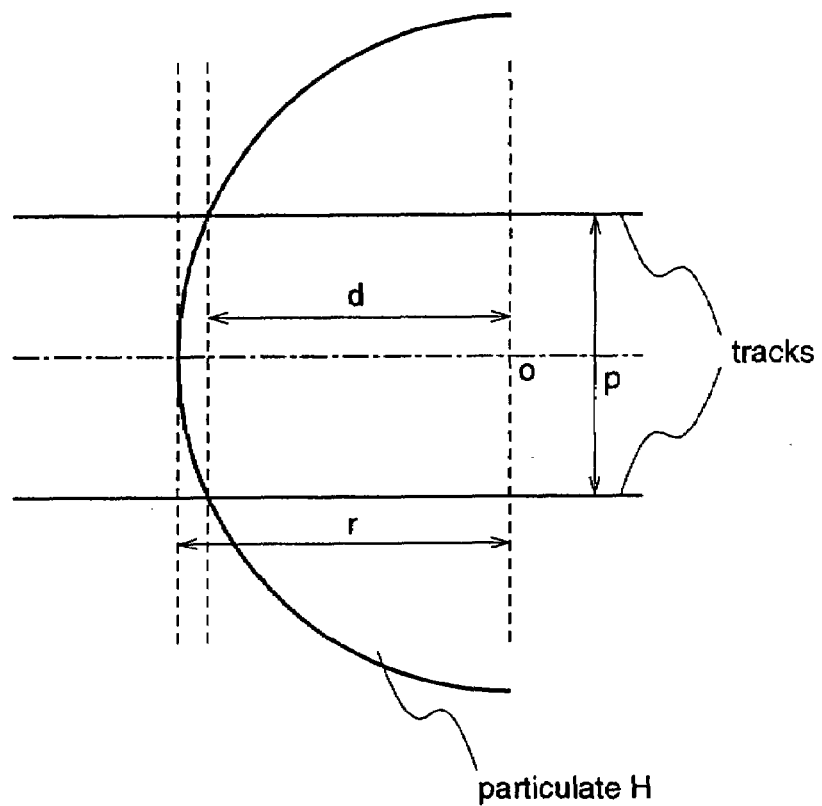
FIG. 16 is a diagram illustrating the relationship between a particulate and tracks in the particulate determination method according to the third embodiment.

Next, a description will be given of a particulate recognition condition in the case where only the particulate H is a target of measurement. FIG. 16 is a diagram illustrating that, among the tracks that intersect the particulate H as a target of measurement, the center of two tracks (alternate long and short dashed line) passes the center o of the particulate, wherein p indicates the track pitch of the optical disc, and r indicates the radius of the particulate H. At this time, the distance d in FIG. 16 can be calculated out from formula (I).

$$d = \sqrt{r^2 - \left(\frac{p}{2}\right)^2} \quad (1)$$

Using 2d that is double the distance d, there is made a recognition condition that the size of the signal pattern in the time-base direction (the distance from a change start position to a change end position in the track direction) is equal to or larger than 2d.

This recognition condition is applied to the S-shaped curves that appear from track 1 to track 16, and 1 is written on the memory array when the result is true, while 0 is written on the memory array when the result is false. Thus generated memory array is shown in FIG. 15.

Next, it is judged that, on the memory array shown in FIG. 15, a portion where plural 1s do not continuously exist in the vertical direction, i.e., a portion where 0s exist above and beneath 1, is a portion where the target particulate exists (judgment criteria A).

As for the particulate G that is not a target of measurement, no 1 exists on the memory array. Further, as for the particulate I that is not a target of measurement, plural 1s continuously exist in the vertical direction. Therefore, these particulates are removed according to the above-mentioned judgment criteria A.

That is, one particulate is detected from the memory array shown in FIG. 15.

In this way, even when plural particulates having different sizes are adjacent to each other, only the target particulate H can be counted.

Next, the particulate recognition condition will be described. As shown in FIG. 16, when the center line between two tracks which pass the particulate passes the center of the particulate, the lengths of the S-shaped curves in the two tracks in the time-base direction (the distances between the change start positions to the change end positions in the track direction) are equal to each other. In this case, when the above-mentioned recognition condition is applied to the lengths of the S-shaped curves in the two tracks in the time-base direction (the distances between the change start positions to the change end positions in the track direction), the respective lengths satisfy formula (1) mentioned above, and therefore, two 1s are written on the memory array.

When the above-mentioned judgment criteria A is applied to this memory array, since plural 1s exist continuously in the vertical direction on the memory array, these is are removed according to the judgment criteria, and are not counted as a particulate. So, when the lengths of adjacent S-shaped curves in the time-base direction are equal to each other, 1 is written on the memory array at only the position corresponding to the initially measured S-shaped curve, while a0, not a1 is written on the memory array at the position corresponding to the S-shaped curve of the same length, which appears next. Thereby, the above-mentioned judgment criteria A becomes applicable, and accurate counting of particulates can be carried out.

As described above, according to the third embodiment, a particulate recognition condition corresponding to the size of a particulate to be detected is previously set, and 1 is written on the memory map only when an S shape larger than the condition is detected. Therefore, even when particulates are adjacent to each other in the vertical direction, plural 1s are not continuously written in the vertical direction, and one particulate can be accurately recognized. Further, by counting only the case where only one 1 stands after window scanning, it is possible to know the size and number of particulates to be detected by onetime scanning.

Embodiment 4

Figure 17:
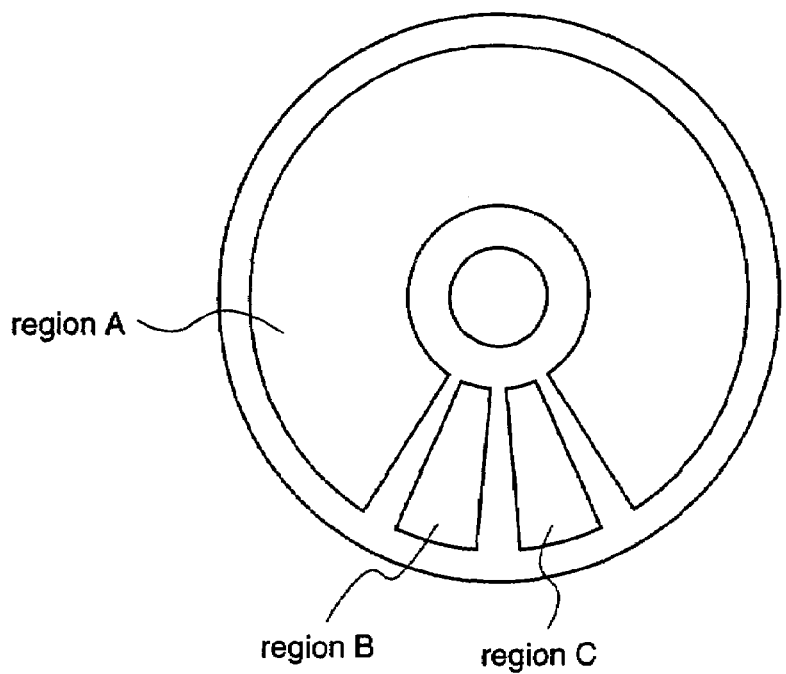
FIG. 17 is a diagram illustrating an example of a layout range of a measurement target on an optical disc, and examples of layout ranges of reference targets for obtaining reference patterns, in a particulate determination method according to a fourth embodiment of the present invention.
Figure 18:
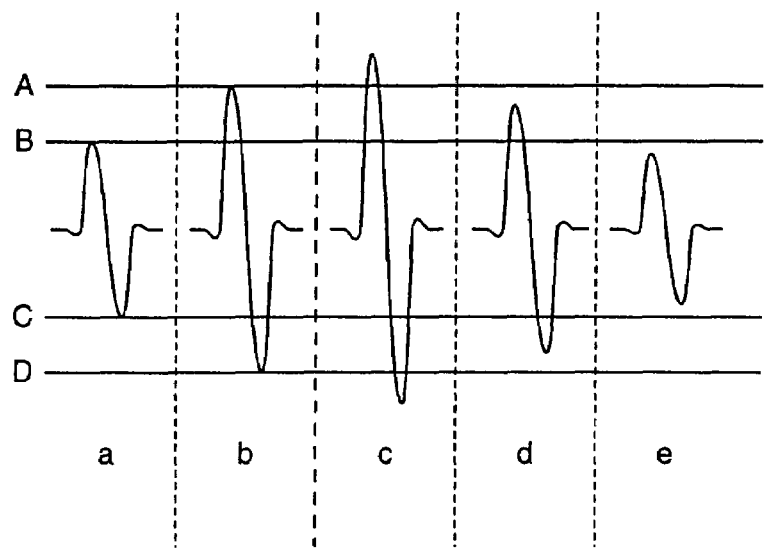
FIG. 18 is a diagram of examples of S-shaped curves which are obtained from the reference targets and the measurement target, in the particulate determination method according to the fourth embodiment.
Figure 19A:
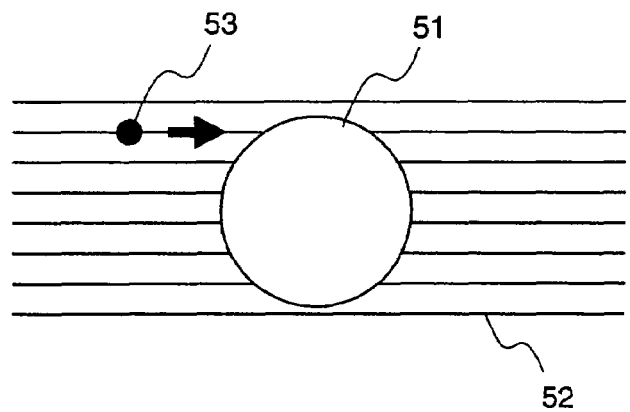
FIG. 19(a) is a diagram illustrating the relationship between a particulate and tracks in the particulate determination method according to the prior art.
Figure 19B:
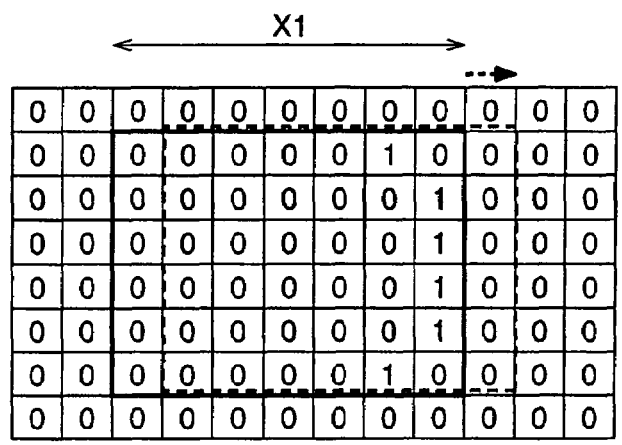
FIG. 19(b) is a diagram of an example of a memory array in the particulate determination method according to the prior art.
Figure 20A:
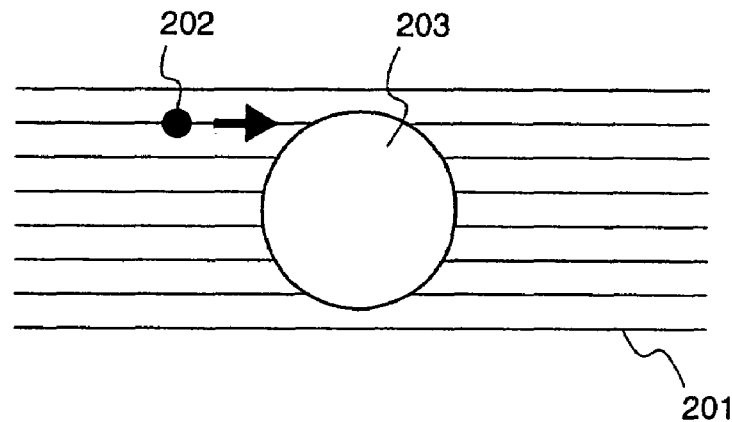
FIG. 20(a) is a diagram illustrating particulate detection in the conventional particulate determination method.
Figure 20B:
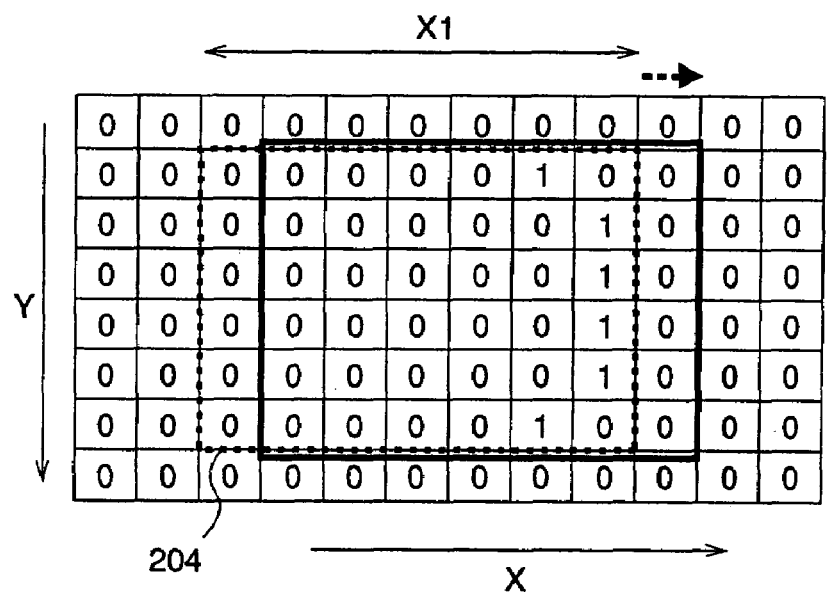
FIG. 20(b) is a diagram illustrating the conventional particulate determination method using a window.

Next, a particulate determination method according to a fourth embodiment of the present invention will be described. FIG. 17 shows examples of a layout range of a target of measurement on an optical disc and layout ranges of reference targets to obtain reference patterns. FIG. 18 shows S-shaped curves obtained from the reference targets and the measurement target.

Further, a block diagram of a device to which the particulate determination method according to the fourth embodiment is applied is identical to the construction shown in FIG. 1 according to the first embodiment.

Hereinafter, characteristic processes in the particulate determination method according to the fourth embodiment will be described.

In FIG. 17, region A shows a layout range of a measurement target, region B shows a layout range of a reference target A having a size that is equal to a minimum value of the size of the measurement target, and region C shows a layout range of a reference target B having a size that is equal to a maximum value of the size of the measurement target.

Before performing counting of the measurement target using such optical disc, S-shaped curves corresponding to the reference target A and the reference target B which are placed in the region B and the region C, respectively, are obtained. In FIG. 18, section "a" shows an S-shaped curve corresponding to the reference target A, and section "b" shows an S-shaped curve corresponding to the reference target B. Then, the maximum levels of amplitudes of the obtained S-shaped curves of the respective reference targets are stored. That is, in FIG. 18, reference line B shows the maximum level of the S-shaped curve corresponding to the reference target A, and reference line A shows the maximum level of the S-shaped curve corresponding to the reference target B.

Likewise, the minimum levels of amplitudes of the S-shaped curves of the respective reference targets are stored. That is, in FIG. 18, reference line C shows the minimum level of the S-shaped curve corresponding to the reference target A, and reference line D shows the minimum level of the S-shaped curve corresponding to the reference target B. Next, an S-shaped curve of the measurement target placed in the region A is obtained using the same method as that described for the first embodiment.

Then, it is judged whether the maximum level or minimum level of the S-shaped curve of the measurement target is within the range of the maximum levels obtained from the reference targets (section between reference lines A and B) or the range of the minimum levels obtained from the reference targets (section between reference lines C and D), respectively. Only when the S-shaped curve obtained from the measurement target is within the range of the maximum levels obtained from the reference targets (section between reference lines A and B) or within the range of the minimum levels obtained from the reference targets (section between reference lines C and D), the process of recording data into the memory, which is the same as those described for the first and second embodiments, is carried out using the S-shaped curve. Moreover, counting of particulates is carried out by the same method as that of the first or second embodiment.

Alternatively, it is judged whether the maximum level and the minimum level of the S-shaped curve of the measurement target are within the range of the maximum levels obtained from the reference targets (section between reference lines A and B) and the range of the minimum levels obtained from the reference targets (section between reference lines C and D), respectively. Only when the S-shaped curve obtained from the measurement target is within the range of the maximum levels obtained from the reference targets (section between reference lines A and B) and within the range of the minimum levels obtained from the reference targets (section between reference lines C and D), the process of recording data into the memory, which is the same as those described for the first and second embodiments, is carried out using the S-shaped curve. Moreover, counting of particulates is carried out by the same method as that of the first or second embodiment.

As described above, the S-shaped curve of the measurement target is selected on the basis of the S-shaped curves of the reference targets, whereby the signals of the S-shaped curves obtained from the targets having the sizes other than that of the measurement target are previously removed. That is, when the S-shaped curves shown in the sections c, d, and e in FIG. 18 are obtained from the measurement target, the data recording process into the memory and the subsequent processes are carried out using only the S-shaped curve shown in the section d. Thereby, accurate counting of particulates can be carried out using only the S-shaped curve signal of the measurement target to be counted.

As described above, according to the fourth embodiment, utilizing the characteristic that the amplitude of a pattern is proportional to the size (diameter) of a target, a maximum value and a minimum value of the size (diameter) of a reference measurement target are previously set on an analysis disc, and distributions of maximum values and minimum values of signals which are obtained by measuring the size of the measurement target are obtained, and then it is determined whether the amplitude of the signal obtained when measuring the measurement target is within the range of the distribution of the maximum values or minimum values of the amplitude of the reference signal, whereby only the desired measurement target can be measured by onetime scanning without measuring the targets having sizes other than the size of the desired target.

Embodiment 5

Figure 21A:
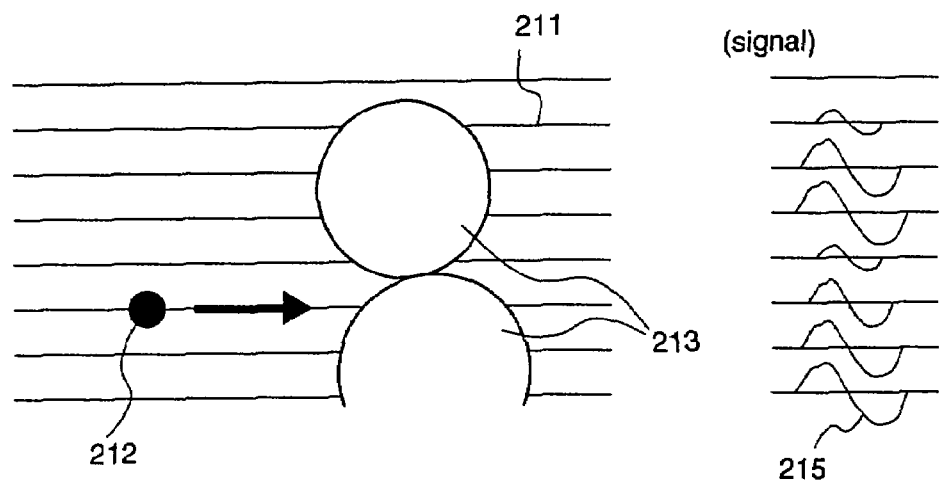
FIG. 21(a) is a diagram illustrating particulate detection in a particulate determination method according to a fifth embodiment of the present invention.

FIG. 21(a) is a diagram illustrating particulate detection in a particulate determination method according to a fifth embodiment of the present invention.

An analysis disc has light reflectivity and permeability, and it is composed of a base disc in which tracks 21 for guiding or data recording are spirally carved, an upper cover having an injection port, and an adhesive layer for bonding the upper cover and the base disc, and forming a flow path.

A specimen for examination is injected into the analysis disc. The specimen passes through the flow path that is constituted by the adhesive layer, passes through the lower surface of the upper cover, and passes through the upper surface of the base disc, and is subjected to pretreatment such as centrifugal separation utilizing. Thus, particulates as measurement target components in the specimen reach an area where measurement should be carried out.

In the measurement area, the particulates in the specimen exist on the surface of the base disc due to a particulate adsorption factor (antibody or the like) that is applied onto the surface of the base disc. The size of each particulate is larger than the width of the track 201, and the particulate lies over plural tracks 201, as shown in FIG. 21(a).

The analysis device has a two-part split PD for receiving a laser beam 212 that has passed through the analysis disc, and a spot of the laser outputted from an optical pickup is positioned in the center of the PD when there is no particulate on the analysis disc.

When a particulate crosses the laser, the position of the laser spot on the PD is changed due to change in refraction of the laser beam, and the position change of the spot is detected as an S-shaped signal by obtaining a difference between the signals from the two-part split PD.

At this time, as shown on the right side of FIG. 21(a), the size of the S-shaped curve 215 changes according to the size of the crossing particulate 213. The larger the crossing particulate 213 is, the larger the S-shaped curve 215 is.

Figure 21B:
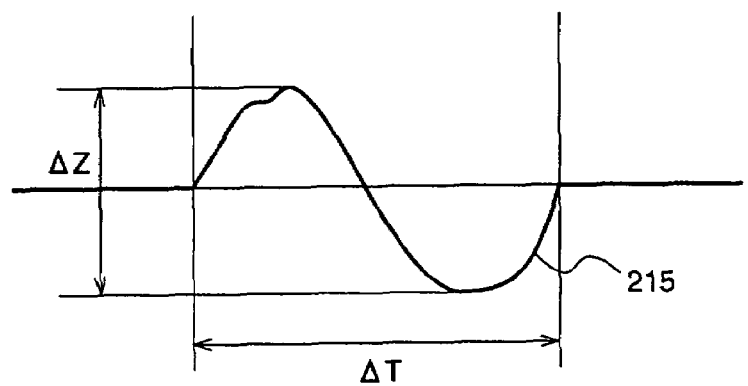
FIG. 21(b) is an enlarged view of an S-shaped curve signal in the particulate determination method according to the fifth embodiment of the present invention.

FIG. 21(b) is a diagram illustrating the enlarged S-shaped curve 215 in the particulate determination method according to the fifth embodiment.

When the S-shaped curve 215 is detected, is are not merely stored in the memory. When the size of the S-shaped curve is judged as being smallest on the basis of the size of $\Delta Z$ or $\Delta T$ shown in FIG. 21(b), "1000" is stored. Then, as the S-shaped curve becomes larger, "1100", "1110" are stored, and "1111" is stored when the S-shaped curve is judged as being largest. In this way, a data array in which the size of the S-shaped curve is divided in several stages is stored in the memory.

Hereinafter, a description will be given of the operation and function with respect to the particulate determination method according to the fifth embodiment of the present invention.

FIG. 22 is a diagram illustrating the particulate determination method according to the fifth embodiment of the present invention.

Figure 22A:
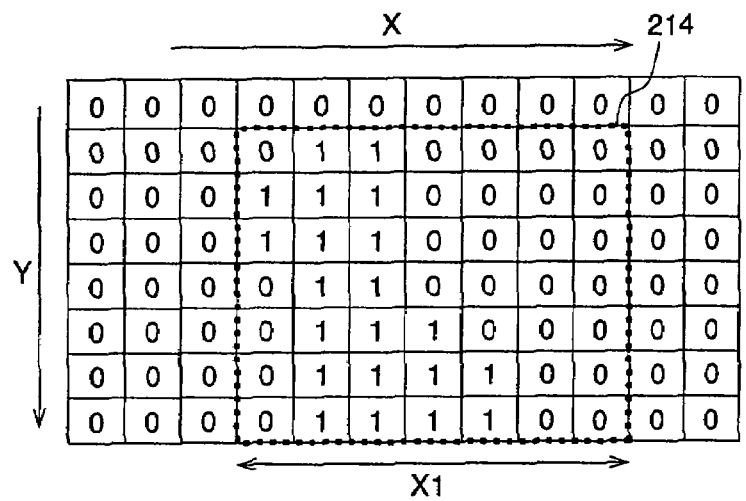
FIG. 22(a) is a diagram illustrating the particulate determination method according to the fifth embodiment of the present invention.

Initially, when detecting a particulate having a size equivalent to seven tracks, as shown in FIG. 22(a), scanning is carried out using an operation (detection) window 214 having a size of 7×X1 while shifting the window one by one in the X direction as the track direction, thereby to detect a portion where the first row of the detection window 214 includes at least one 1.

When a 1 is detected, the detection window 214 is shifted one by one in the track direction while monitoring the total number of 1s in each row, and finally, the detection window 214 is shifted to a position where the number of 1s in each row does not change even when the detection window 214 is shifted in the track direction.

The state where the number of 1s in each row does not change even when the detection window 214 is shifted in the track direction indicates that all the is around the detection window are enclosed in the detection window.

Next, at the position thus detected, it is judged whether or not each of the rows in the window having the size of 7×X1 includes one or more 1s.

When any of the rows does not include 1, the size of the particulate is judged as being smaller than seven tracks, and this particulate is not counted.

Figure 22B:
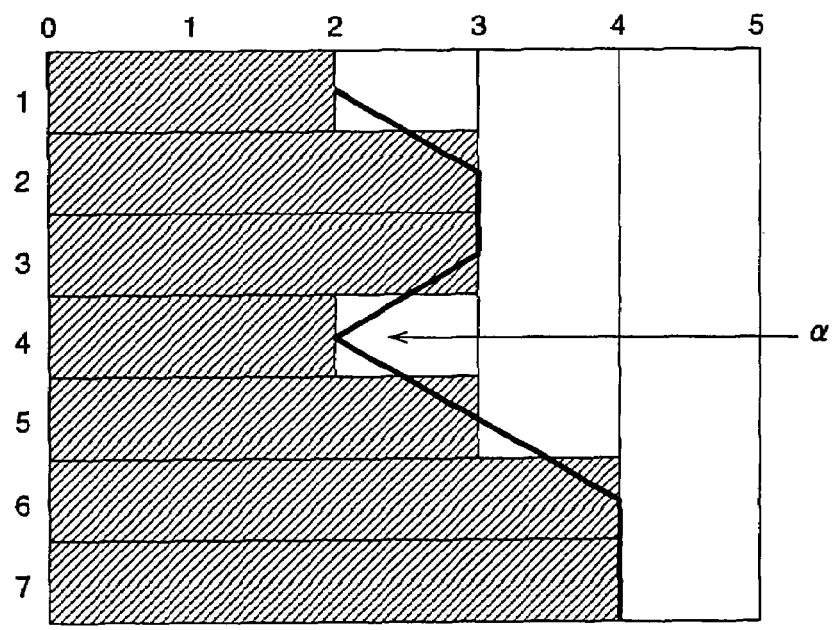
FIG. 22(b) is a graph expressing the number of 1s which are detected in a window in the particulate determination method according to the fifth embodiment of the present invention.

When each of the rows in the window having the size of 7 X1 includes one or more is, increase or decrease of the number of 1s in each track is checked. As shown in FIG. 22(b), when there is a portion where a constriction as shown by a occurs, it is judged that there are plural particulates, and these particulates are counted separately.

Further, even though no constriction occurs, when there is a portion where the number of 1s constant without increase or decrease, it is judged that a plurality of small particulates are arranged, and another counting should be carried out.

As for 1s in once-read positions, these is are deleted from the memory, and next window scanning is carried out. The number of particulates having sizes equal to or larger than seven tracks can be calculated by taking a difference between the number of particulates obtained in the first scanning and that obtained in the second scanning.

When the scanning using the window having the size of 7×X1 is ended, scanning is carried out using a window having a size of 8×X1 while shifting the window one by one in the X direction. Since is are deleted from the memory in the previous scanning, S-shape detection is again carried out, and the detected S-shaped curve is stored in the memory.

Then, scanning is carried out using the window having the size of 8×X1 while shifting the window one by one in the X direction, and thereafter, the same processing as that for the 7×X1 window is carried out.

Through a series of window operations described above, it is possible to detect the number of particulates having the sizes equivalent to or larger than seven tracks, the number of particulates having the sizes equivalent to or larger than eight tracks, and the number of particulates each comprising a plurality of particulates. Moreover, the number of particulates having the size equivalent to seven tracks can be obtained by taking a difference.

While in this fifth embodiment the array of 1s is represented by four lines of four stages "1000"~"1111", it may be represented by five lines ("10000"~"11111") or six lines ("100000"~"111111") to improve resolution, with the same effects as mentioned above.

As described above, in the particulate determination method according to the fifth embodiment, the analysis disc into which a plurality of particulates 213 are injected is irradiated with the laser beam 212, the laser beam 212 is detected with the PD, and the detected signal is subjected to data processing and stored in the memory to determine independence of each particulate. This, method also includes a step of storing, into the memory, an array of binary data comprising 0s and 1s, which is determined on the basis of the presence or absence of a particulate 213 and the size of the particulate 213, and a step of determining the size of the particulate from the data arrays in the track direction and the radial direction of the analysis disc. When an S-shaped curve 215 is detected, the size of the S-shaped curve 215 is divided into several stages, and information indicating the size of the S-shaped curve 215 is added to the data array on the memory. Therefore, it is possible to judge whether the particulate comprises a plurality of particulates or a single particulate, whereby a more accurate number of particulates can be obtained.

Embodiment 6

Figure 23A:
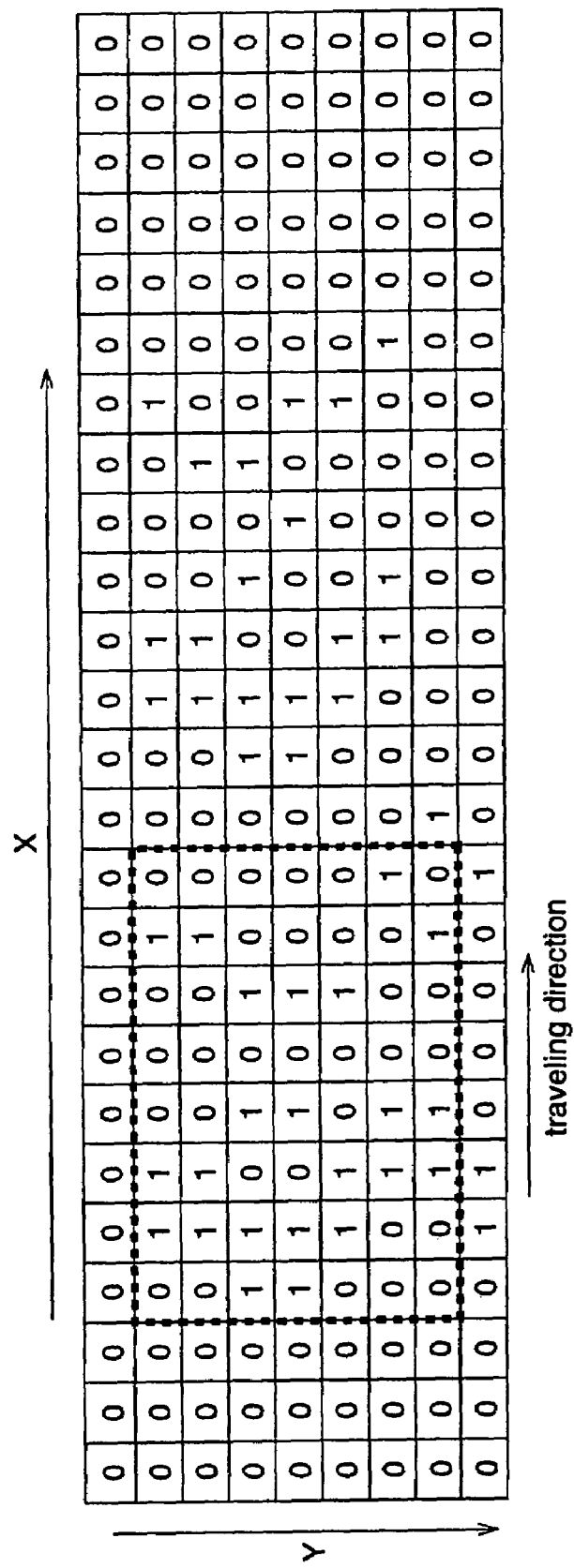
FIG. 23(a) is a diagram illustrating a particulate determination method according to a sixth embodiment of the present invention.
Figure 23B:
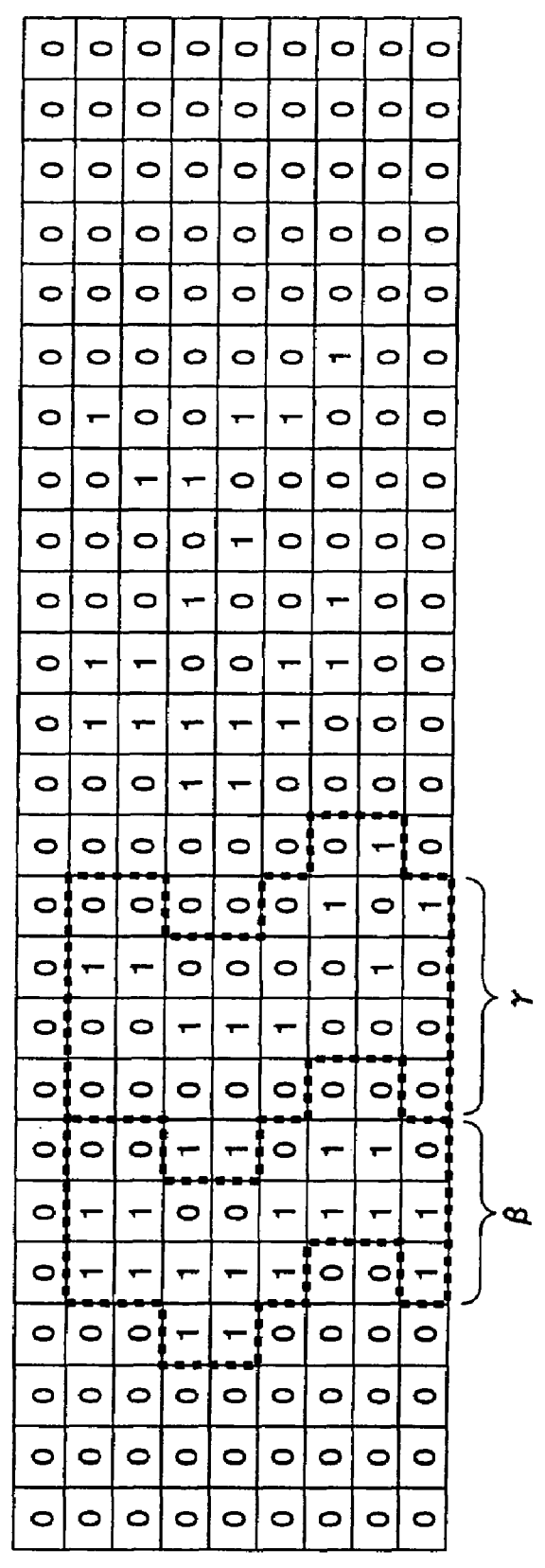

FIG. 23(a) is a diagram illustrating a particulate determination method according to a sixth embodiment of the present invention, and FIG. 23(b) is a diagram illustrating a data array stored in a memory.

Since a method for detecting a particulate according to the sixth embodiment is identical to that of the first embodiment, repeated description is not necessary. This sixth embodiment is different from the first embodiment in that a data array indicating the presence or absence of a particulate is "11", and "110" is stored for window detection in the memory when an S-shaped curve is detected. The size of the S-shaped curve is divided into several stages, and further, "0001" is stored in the memory when it is judged that there is a particulate of the smallest S-shaped curve, while "1010" is stored in the memory when it is judged that there is a particulate of the largest S-shaped curve. That is, the stages are assigned to arrays of 1s and 0s in which continuous 1s do not exist.

For example, assuming that the array indicating the size of the S-shaped curve comprises four digits, the size of the S-shaped curve can be classified into eight stages 0, 1, 2, 4, 5, 8, 9, and 10.

As described above, since the array indicating the presence or absence of a particulate is separated from the array indicating the size of the S-shaped curve, it becomes unnecessary in the position detection step to keep a watch on the number of 1s in each row in the window. Therefore, the operation of the detection window is not complicated as compared with that of the first embodiment.

Further, in the case of four digits, the number of divided stages is seven and eight, which is not very much different from that of the fifth embodiment. However, in the case of five digits, the number of divided stages is thirteen, which is five stages larger than that of the fifth embodiment, and therefore, it is advantageous for fine classification.

Hereinafter, a description will be given of the operation and function of the particulate determination method according to the sixth embodiment constituted as described above.

Initially, when detecting a particulate having a size equivalent to seven tracks, scanning is carried out using a window 214 having a size of 7×X1 shown in FIG. 23(a), while shifting the window one by one in the X direction as the track direction, and positions where all rows include "11" as shown by the range β in FIG. 23(b) are counted.

When the compatibility condition is satisfied, the data are further analyzed with respect to the range γ shown in FIG. 23(b). When there is a tendency that the size of the S-shaped curve decreases in some midpoint in the rows in the window, it is judged that plural particulates exist, and these particulates are counted separately.

Once-read is are deleted from the memory to present one particulate from being counted twice, and S shape detection is again carried out before performing scanning using another window, and detected S-shape curves are stored in the memory.

Next, similar scanning is carried out using a window having a size of 8×X1, and positions where all of the rows in the window include "11" are counted, and further, positions where the size of the S-shaped curve tends to decrease at some midpoint in the rows in the window are counted.

Through a series of window operations described above, it is possible to detect the number of particulates having the sizes equivalent to or larger than seven tracks, the number of particulates having the sizes equivalent to or larger than eight tracks, and the number of particulates each comprising a plurality of particulates. Moreover, the number of particulates having the size equivalent to seven tracks can be obtained by taking a difference.

While in this sixth embodiment the data array indicating the size of the S-shaped curve is composed of four digits, it may be composed of five, six, . . . digits to improve resolution, with the same effects as described above.

Further, even when the data array is composed of three digits, the size of the S-shaped curve can be classified into five stages. Even three digits are adequate for determining whether there are a plurality of particulates or not.

As described above, in the particulate determination method according to the sixth embodiment, the analysis disc into which a plurality of particulates 213 are injected is irradiated with the laser beam 212. The laser beam 212 is detected with the PD, and the detected signal is subjected to data processing and stored in the memory to determine independence of each particulate. This method also includes a step of writing "0" on the memory in a position next to "11" that is a data array indicating the presence or absence of the particulate 3, and a step of writing, on the memory, the data array which is encoded on the basis of the size of an S-shaped curve that is detected by the PD when the laser beam 2 crosses the particulate 3. When an S-shaped curve is detected, the size of the S-shaped curve is divided into several stages. Information indicating the size of the S-shaped curve is added to the data array on the memory, in addition to the information indicating presence/absence of the S-shaped curve. Therefore, the operation of the detection window is simplified, and it is possible to detect whether the particulate comprises a plurality of particulates or a single particulate, whereby more accurate number of particulates can be obtained.

Embodiment 7

Figures 24A, 24B:
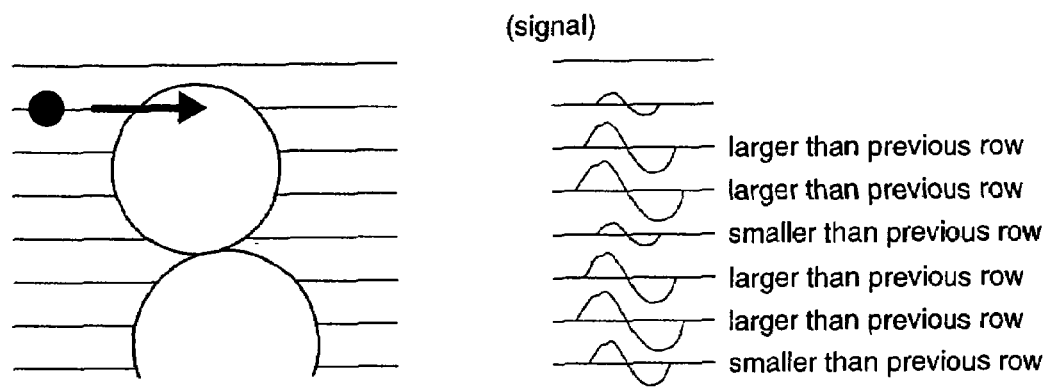
FIG. 24(a) is a diagram illustrating a particulate determination method according to a seventh embodiment of the present invention.

FIG. 24(a) is a diagram illustrating a particulate determination method according to a seventh embodiment of the present invention, and FIG. 24(b) is a diagram illustrating a data array stored in a memory. In FIG. 24(b), the data array in the vertical direction indicates the radius of a particulate.

In contrast to the fifth and sixth embodiments, this seventh embodiment is provided with a routine in which, when an S-shaped curve is detected, the size of the detected S-shaped curve is compared with the size of an S-shaped curve of the previous row. When the S-shaped curve of the previous row is larger than the detected S-shaped curve, no array is stored on the memory. After detection of the S-shaped curve, the presence or absence of a particulate is checked in the data array in the previous row.

If there is no particulate in the previous row, "110" is stored for window detection in the memory. Next, the size of the S-shaped curve is classified into several stages. Furthermore, the stages are assigned to data arrays of 1s and 0s in which continuous 1s do not exist, and a data array suited to the size of the S-shaped curve, which is detected from among the data arrays, is stored in the memory.

For example, assuming that the array indicating the size of the S-shaped curve comprises four digits, the size of the S-shaped curve can be classified into eight stages "0000", "0001", "0010", "0100", "0101", "1000", "1001", and "1010".

When an S-shaped curve is detected in the next row, the presence or absence of a particulate in the previous row is checked.

Then, the data array indicating the size of the S-shaped curve of the previous row is compared with the detected S-shaped curve. When the detected S-shaped curve is larger than the S-shaped curve of the previous row, "110" is stored for window detection in the memory. Next, the size of the S-shaped curve is classified into several stages. Furthermore, the stages are assigned to data arrays of 1s and 0s in which continuous 1s do not exist, and a data array suited to the size of the S-shaped curve, which is detected from among the data arrays, is stored in the memory.

If the detected S-shaped curve is smaller than the S-shaped curve of the previous row, the data array indicating the presence or absence of the S-shaped curve and the size of the S-shaped curve is not stored on the memory.

As described above, in the particulate determination method according to the seventh embodiment, when particulates having sizes equivalent to 6~7 tracks are to be detected, initially, detection of array in which "11" continues over three or more rows on the memory is carried out using a window having a size of 3×X1.

After detecting particulates having sizes equivalent to 6 or more tracks using the window of 3×X1, particulates having sizes equivalent to 8 or more tracks are detected using a window having a size of 4×X1.

Then, the number of particulates having the sizes equivalent to 6 or more tracks are subtracted from the number of particulates having the sizes equivalent to 8 or more tracks, whereby particulates having the sizes equivalent to 6~7 tracks can be detected.

As described above, in the particulate determination method according to the seventh embodiment, the analysis disc into which a plurality of particulates 213 are injected is irradiated with the laser beam 212, the laser beam 212 is detected with the PD, and the detected signal is subjected to data processing and stored in the memory to determine independence of each particulate. In this method, when the S-shaped curve of the data array obtained during particulate detection is smaller than that of the data array in the previous row, data is not stored on the memory. Since no data array is stored on the memory when the detected S-shaped curve is smaller than the S-shaped curve in the previous row, even when there exist a plurality of particulates adjacent to each other, data are not connected in the vertical direction but are clearly distinguished, whereby more accurate number of particulates can be obtained.

A particulate determination method according to the present invention has an effect that a plurality of particulates that are continuous in the radial direction of a disc can be counted without false recognition. The method is also useful as, for example, a particulate counting method employed by an analysis device for counting the number of analysis targets. Further, even when a plurality of particulates are adjacent to each other, the particulate determination method can accurately determine each particulate as a target and therefore, it is useful for measuring each target, and determining the number of targets.

What is claimed is:

1. A method for determining independence of a particulate as a measurement target which is injected into an analysis disc, said method including:

storing, into a memory, an array of binary data comprising 0s and 1s, which is determined on a basis of a presence or absence of the particulate and a size of the particulate;

determining the size of the particulate on the basis of the data array in a track direction and a radius direction of the analysis disc; and judging that there are plural particulates when it is detected that 1s continue in the data array in the radius direction, and the number of 1s in the data array in the track direction decreases at least one of a plurality of rows of the data array.

2. A method for determining independence of a particulate as a measurement target in accordance with claim 1 wherein the data array in the track direction has a larger number of 1s when an S-shaped curve, which is a particulate detection signal and has a maximum value and a minimum value, is large, and has a smaller number of 1s when the S-shaped curve is small.

3. The method for determining independence of a particulate as a measurement target in accordance with claim 1, said method further comprising writing a second data array based on a size of an S-shaped curve which is a particulate detection signal and has a maximum value and a minimum value, on a memory, in a position next to the data array indicating the presence or absence of the particulate.

4. A method for determining independence of a particulate as a measurement target in accordance with claim 3 wherein continuous 1s do not exist in the second data array.

5. A method for determining independence of a particulate as a measurement target in accordance with claim 3 which is realized by a particulate determination device comprising:

an optical pickup which is provided movably with respect to the analysis disc, and comprises an optical system including a light source, an objective lens, an actuator for driving the objective lens in a rotation axis direction and a radius direction of the analysis disc, and a photodetector for converting a reflected light from the analysis disc into electricity;

a spindle motor as a rotation driving means for the analysis disc;

a servo control circuit for performing focus servo control, tracking servo control, and spindle servo control on a basis of a signal outputted from the optical pickup;

a photo detector (PD) for receiving a laser light which has been emitted from the optical pickup and has passed through the analysis disc, and converting the light into electricity;

an S-shaped curve detection circuit for detecting an S-shaped curve on a basis of an electric signal outputted from the PD;

a memory for holding an array of binary data which is processed on a basis of an output signal from the S-shaped curve detection circuit; and a particulate recognition circuit for recognizing a particulate on a basis of data stored in the memory.

6. A method for determining independence of a particulate as a measurement target in accordance with claim 1 which is realized by a particulate determination device comprising:

an optical pickup which is provided movably with respect to the analysis disc, and comprises an optical system including a light source, an objective lens, an actuator for driving the objective lens in a rotation axis direction and a radius direction of the analysis disc, and a photodetector for converting a reflected light from the analysis disc into electricity;

a spindle motor as a rotation driving means for the analysis disc;

a servo control circuit for performing focus servo control, tracking servo control, and spindle servo control on a basis of a signal outputted from the optical pickup;

a photo detector (PD) for receiving a laser light which has been emitted from the optical pickup and has passed through the analysis disc, and converting the light into electricity;

an S-shaped curve detection circuit for detecting an S-shaped curve on a basis of an electric signal outputted from the PD;

a memory for holding an array of binary data which is processed on a basis of an output signal from the S-shaped curve detection circuit; and a particulate recognition circuit for recognizing a particulate on a basis of data stored in the memory.

7. A method for determining independence of a particulate as a measurement target which is injected into an analysis disc, said method including:

storing, into a memory, an array of binary data comprising 0s and 1s, which is determined on a basis of a presence or absence of the particulate and a size of the particulate;

determining the size of the particulate on the basis of the data array in a track direction and a radius direction of the analysis disc; and determining that there are plural particulates when 1s continue in the data array in the radius direction, and the number of 1s in the data array in the track direction is the same in each of a plurality of rows of the data array.

* * * * *